United States Patent
Takano

(10) Patent No.: US 7,506,544 B2
(45) Date of Patent: Mar. 24, 2009

(54) FUNCTIONAL DIAGRAM FOR MUSCLE AND MUSCLE STRENGTH REFLEX TEST AND EXAMINATION METHOD USING THE SAME

(76) Inventor: Kihachirou Takano, 198-1, Ro, Asahi-shi, Chiba-ken (JP)

( * ) Notice: Subject to any disclaimer, the term of this patent is extended or adjusted under 35 U.S.C. 154(b) by 0 days.

(21) Appl. No.: 11/775,645

(22) Filed: Jul. 10, 2007

(65) Prior Publication Data
US 2008/0047342 A1    Feb. 28, 2008

(30) Foreign Application Priority Data
Jul. 11, 2006    (JP)    ................. 2006-005551

(51) Int. Cl.
*A61B 5/22*    (2006.01)
(52) U.S. Cl. ............................... 73/379.01
(58) Field of Classification Search .......... 73/379.01, 73/379.02; 600/300, 301; 378/41
See application file for complete search history.

(56) References Cited

U.S. PATENT DOCUMENTS 5,090,038 A * 2/1992 Asahina ................. 378/41
5,188,107 A   2/1993 Omura
6,884,214 B2 * 4/2005 Itagaki ................. 600/300

FOREIGN PATENT DOCUMENTS
JP    2003-310576    11/2003
JP    2005-261881    9/2005

* cited by examiner

*Primary Examiner*—Jewel Thompson
(74) *Attorney, Agent, or Firm*—Rabin & Berdo, P.C.

(57) ABSTRACT

A functional diagram for a muscle and muscle strength reflex test is provided to enable a chiropractic practitioner or the like to easily diagnose an unknown disease and the cause of the disease. The functional diagram comprises an image portion identifying a prescribed examination item and a scale portion arranged adjacent to the image portion and having a scale representing a degree of the examination item. Furthermore, an examination method for examining a patient with the use of a functional diagram for a muscle and muscle strength reflex test is provided. The examination method comprises the steps of having a patient touch a portion of the functional diagram representing a portion or symptom of his body with one of his fingers of one of his hands and having a patient undergo the muscle and muscle strength reflex test to examine the portion or symptom of his body represented by the portion of the functional diagram touched by the patient.

5 Claims, 44 Drawing Sheets

FUNCTIONAL DIAGRAM OF LEG LENGTH

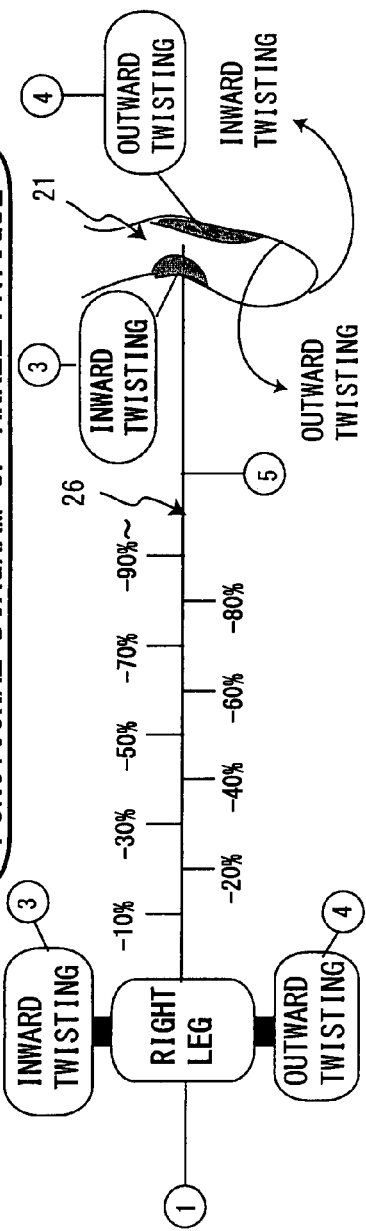
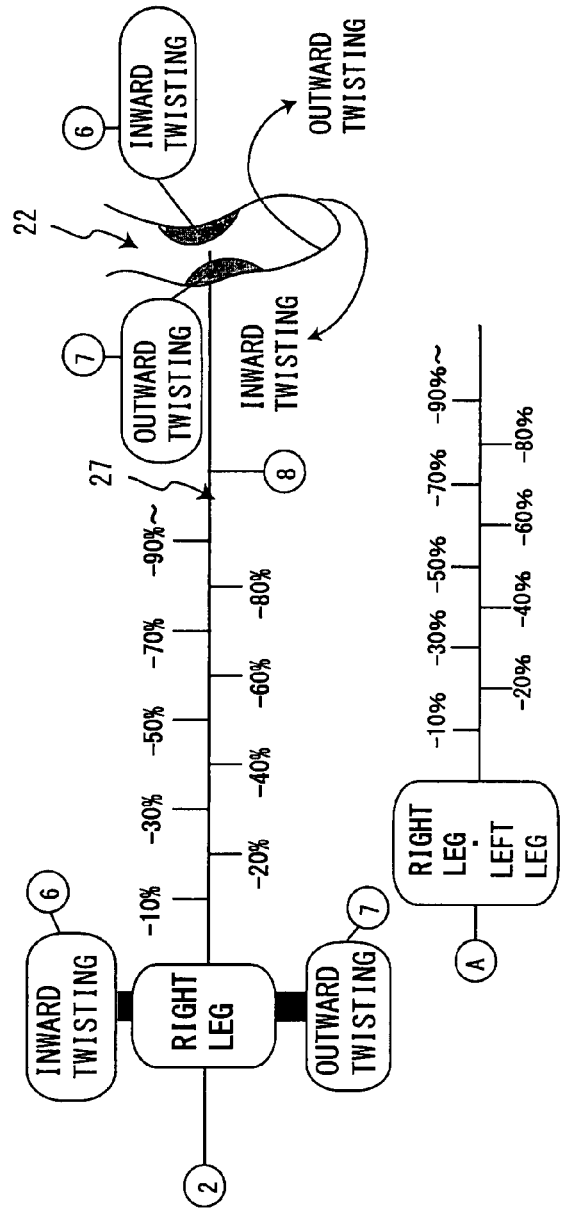
FIG. 2 FUNCTIONAL DIAGRAM OF ANKLE FATIGUE

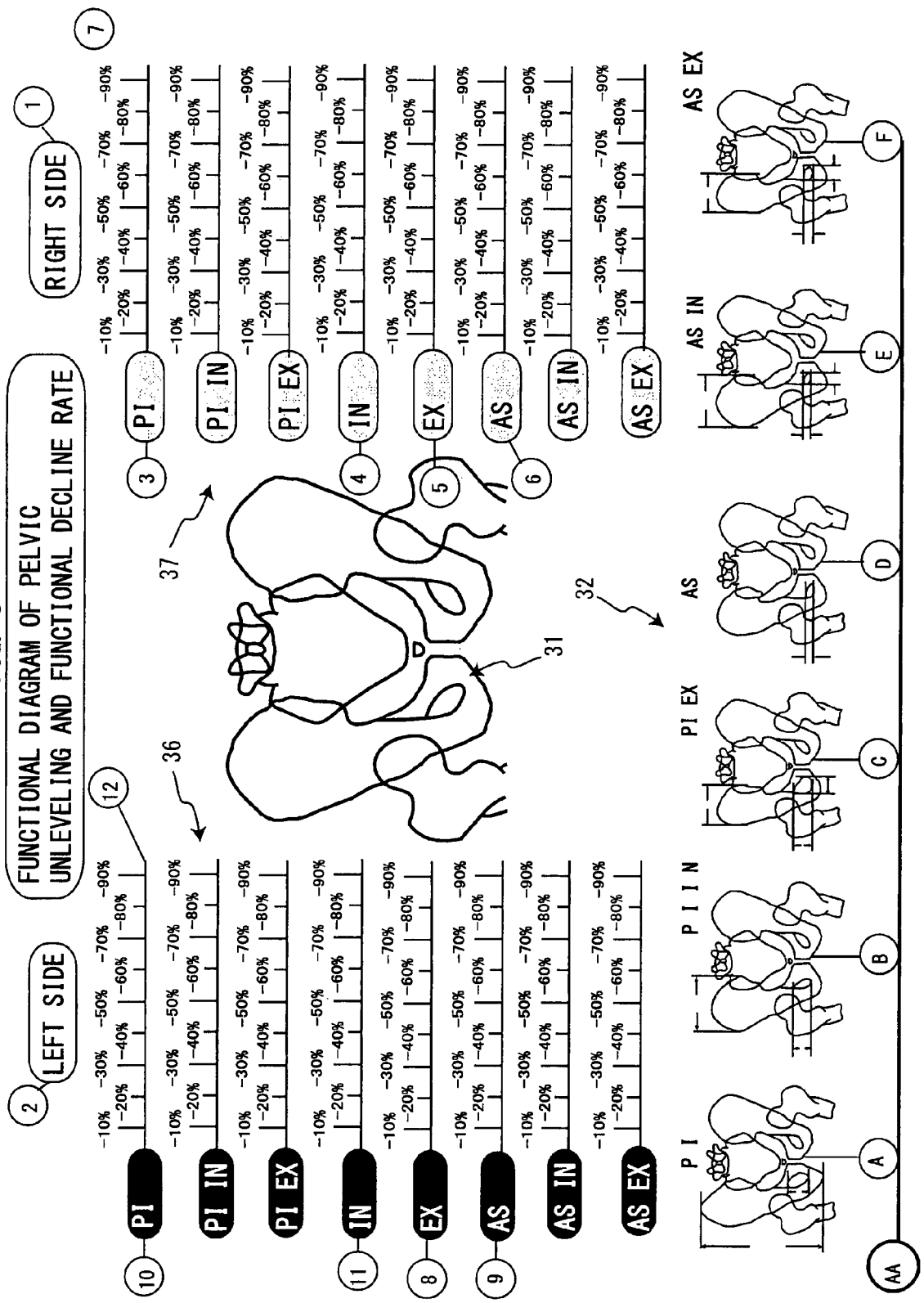

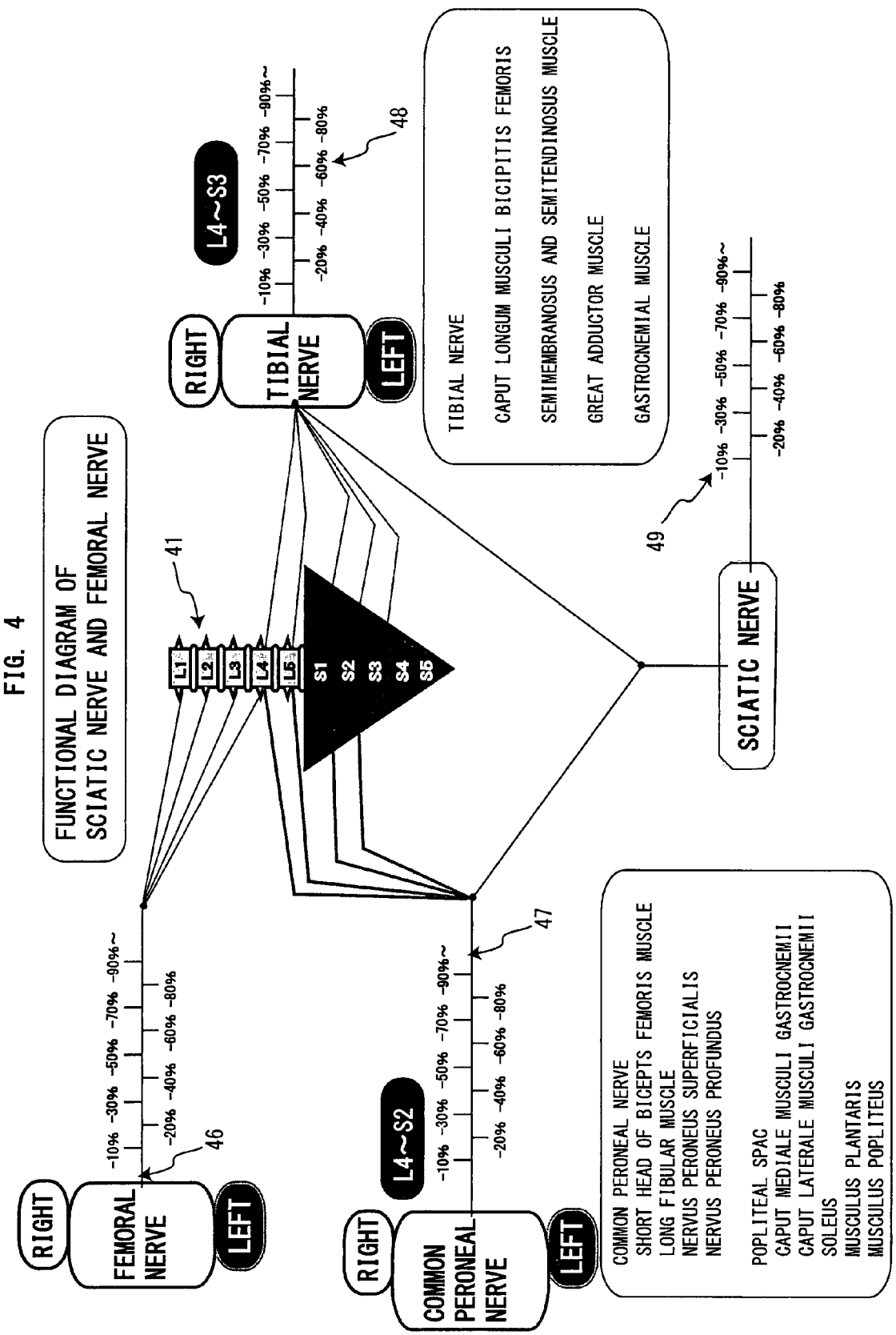

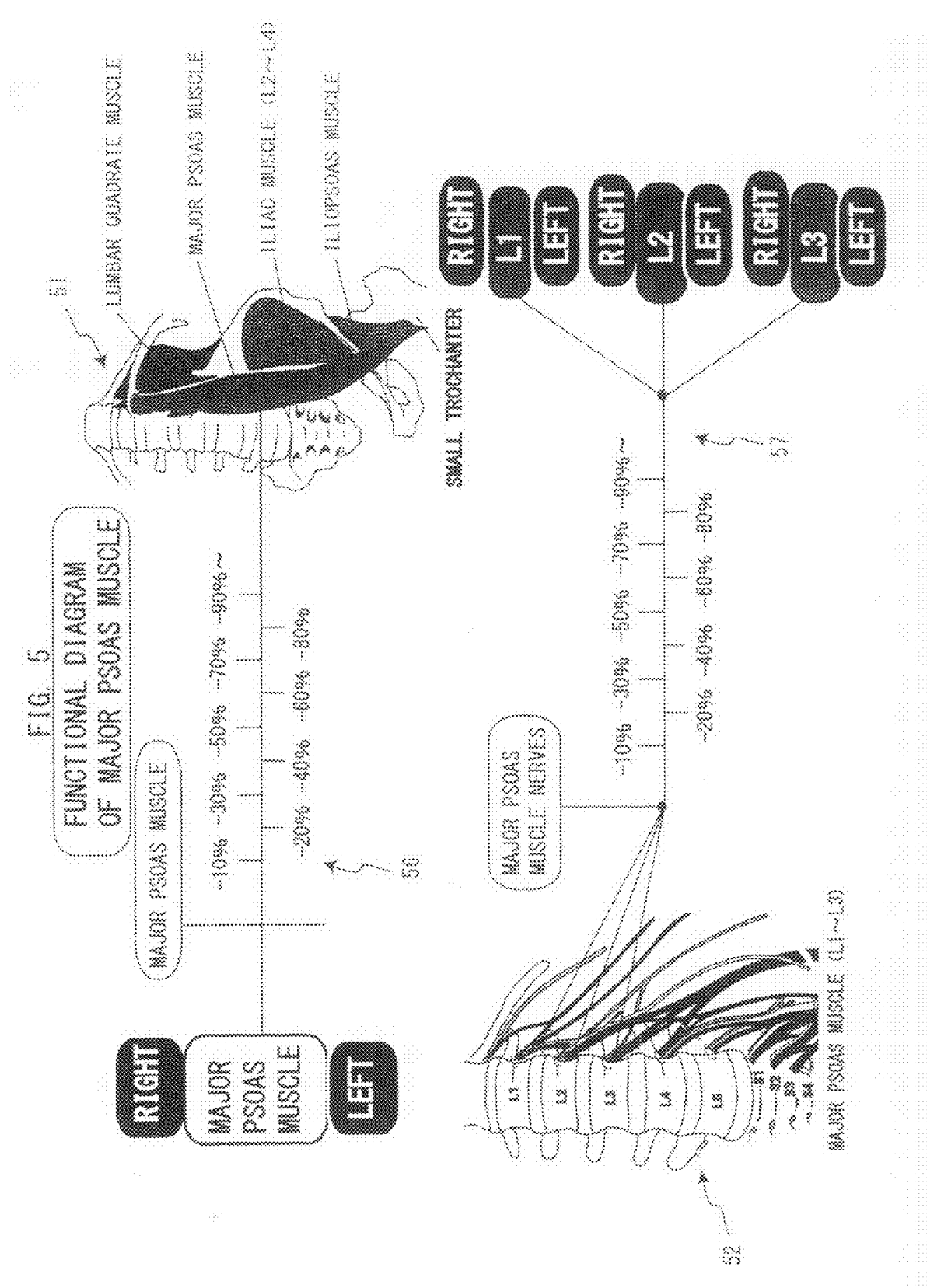

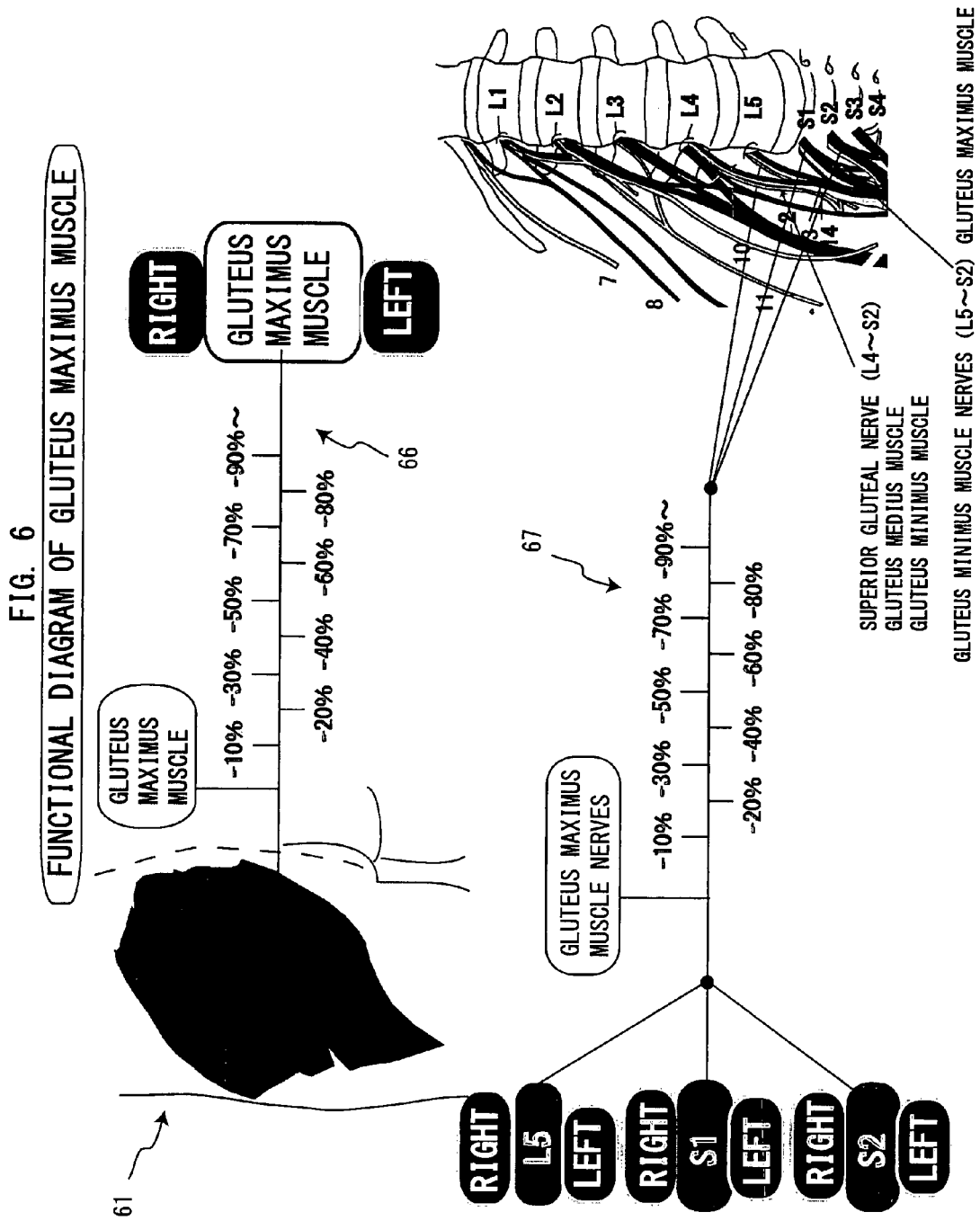

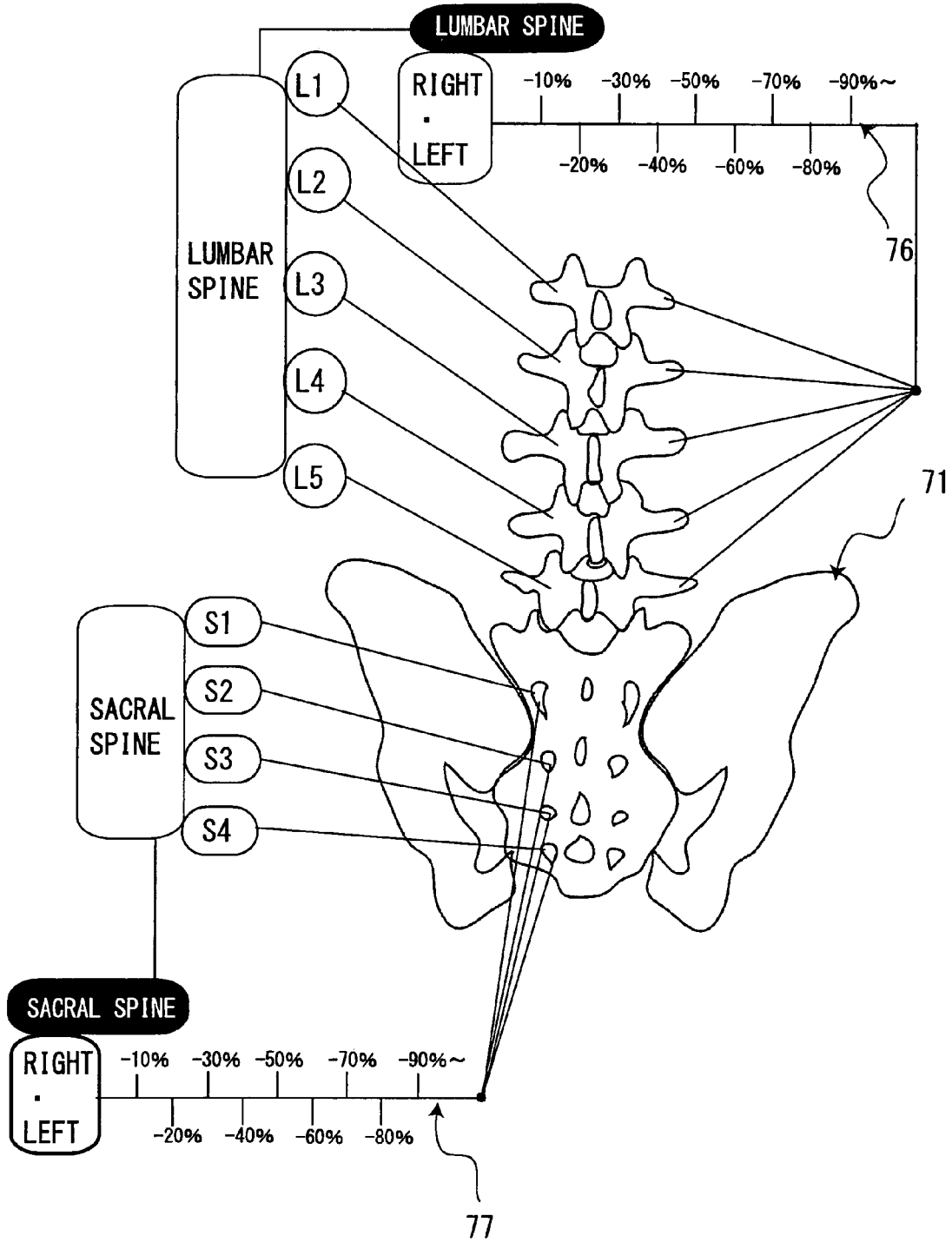

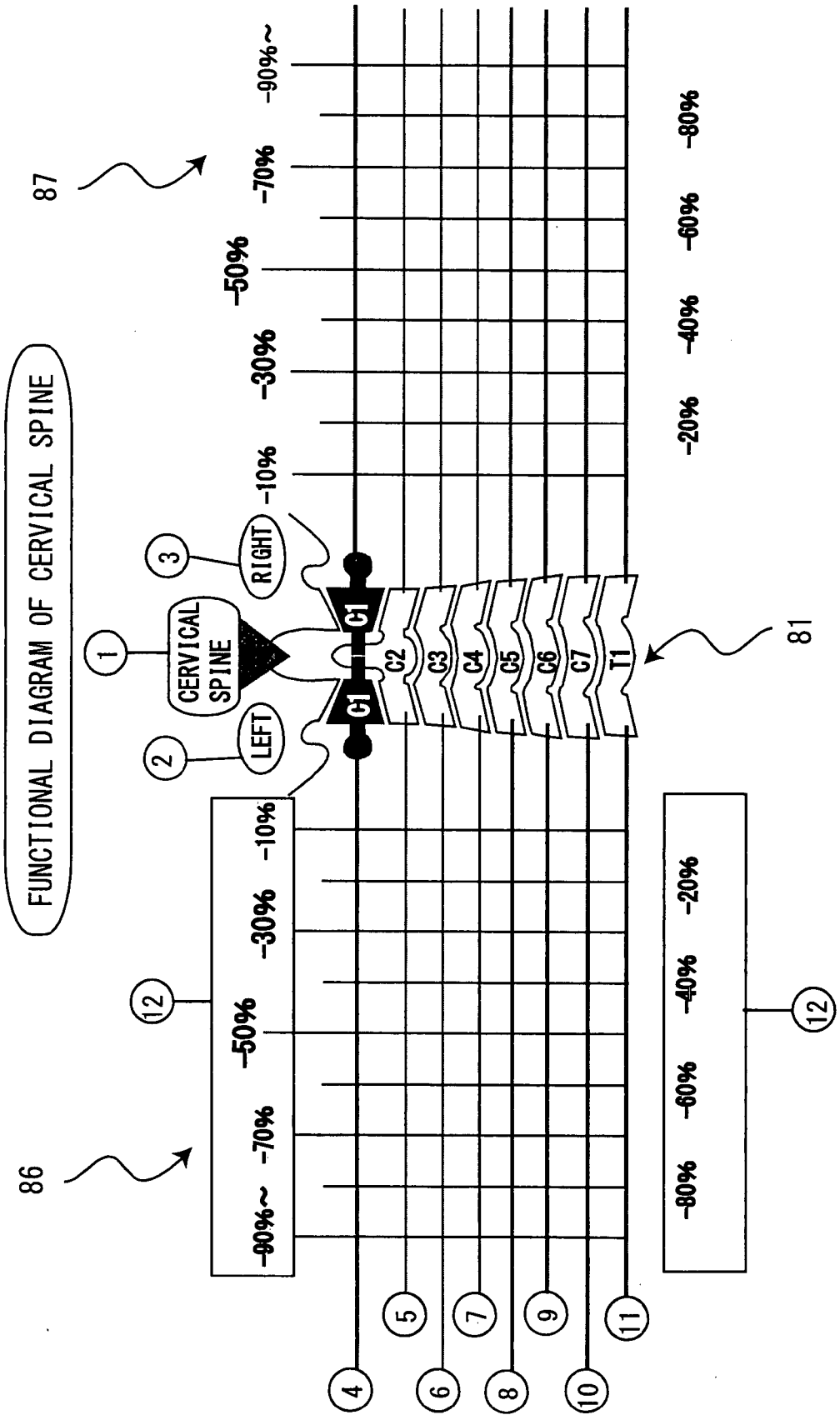
FIG. 8 FUNCTIONAL DIAGRAM OF CERVICAL SPINE

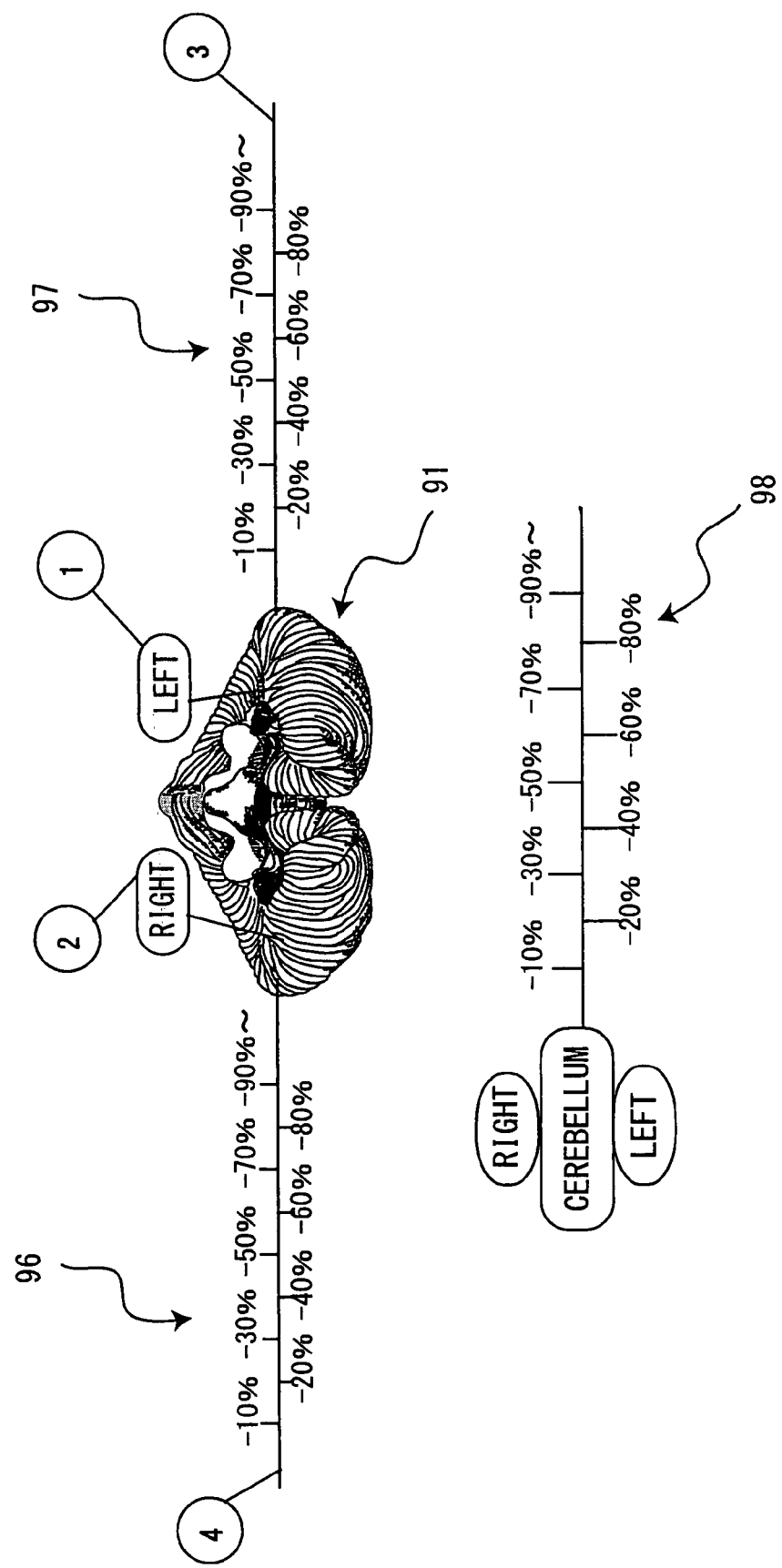

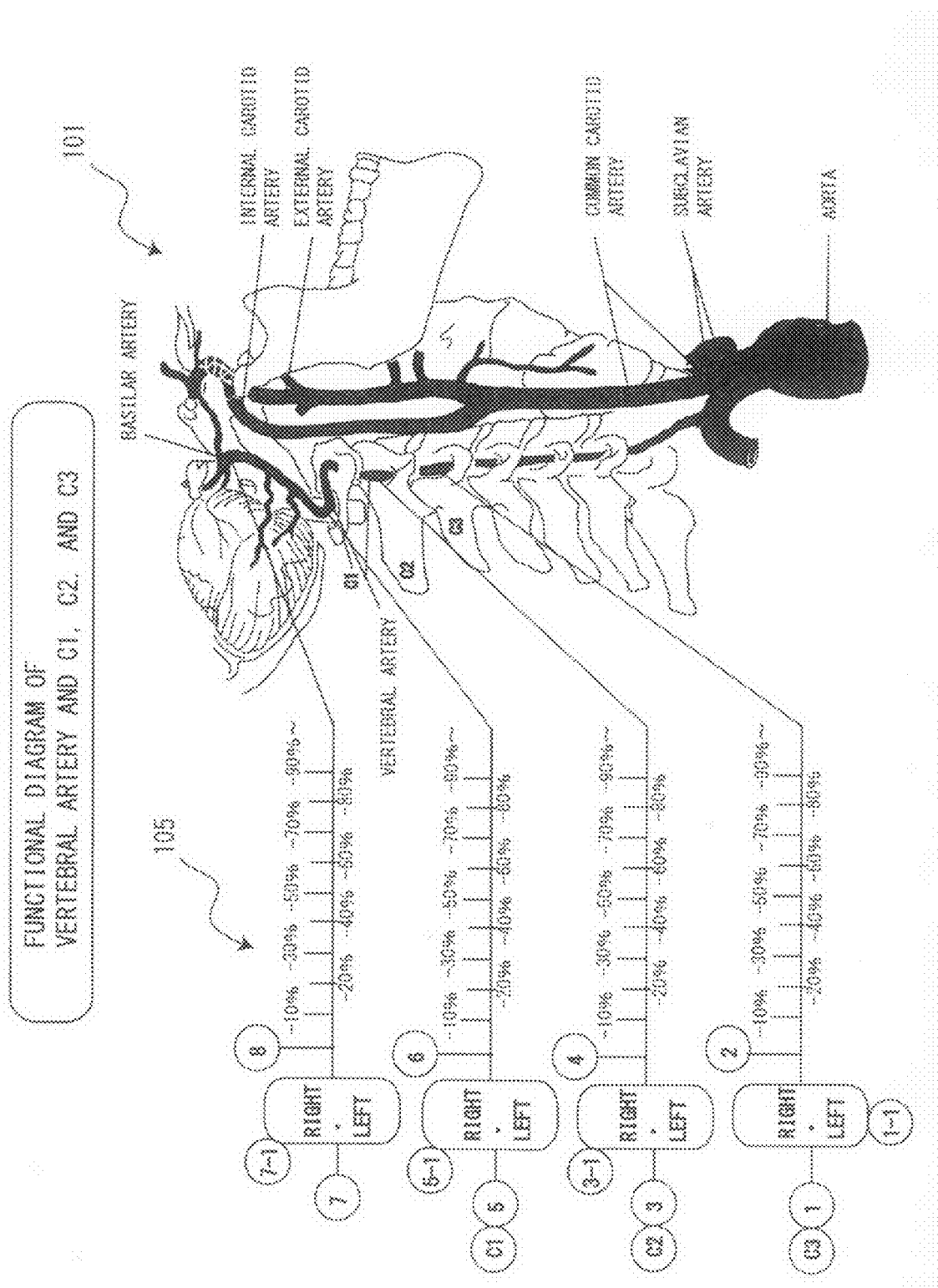

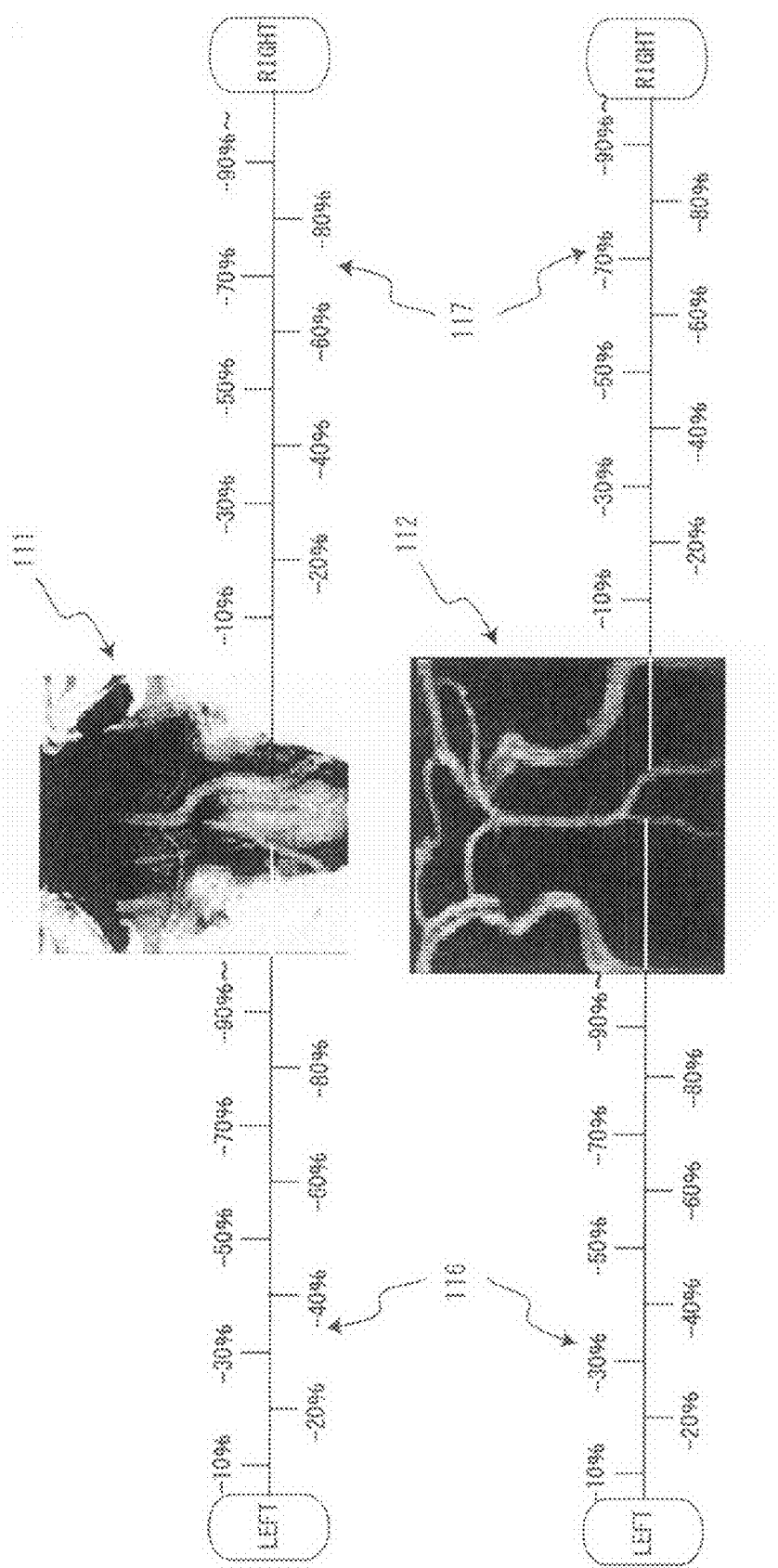

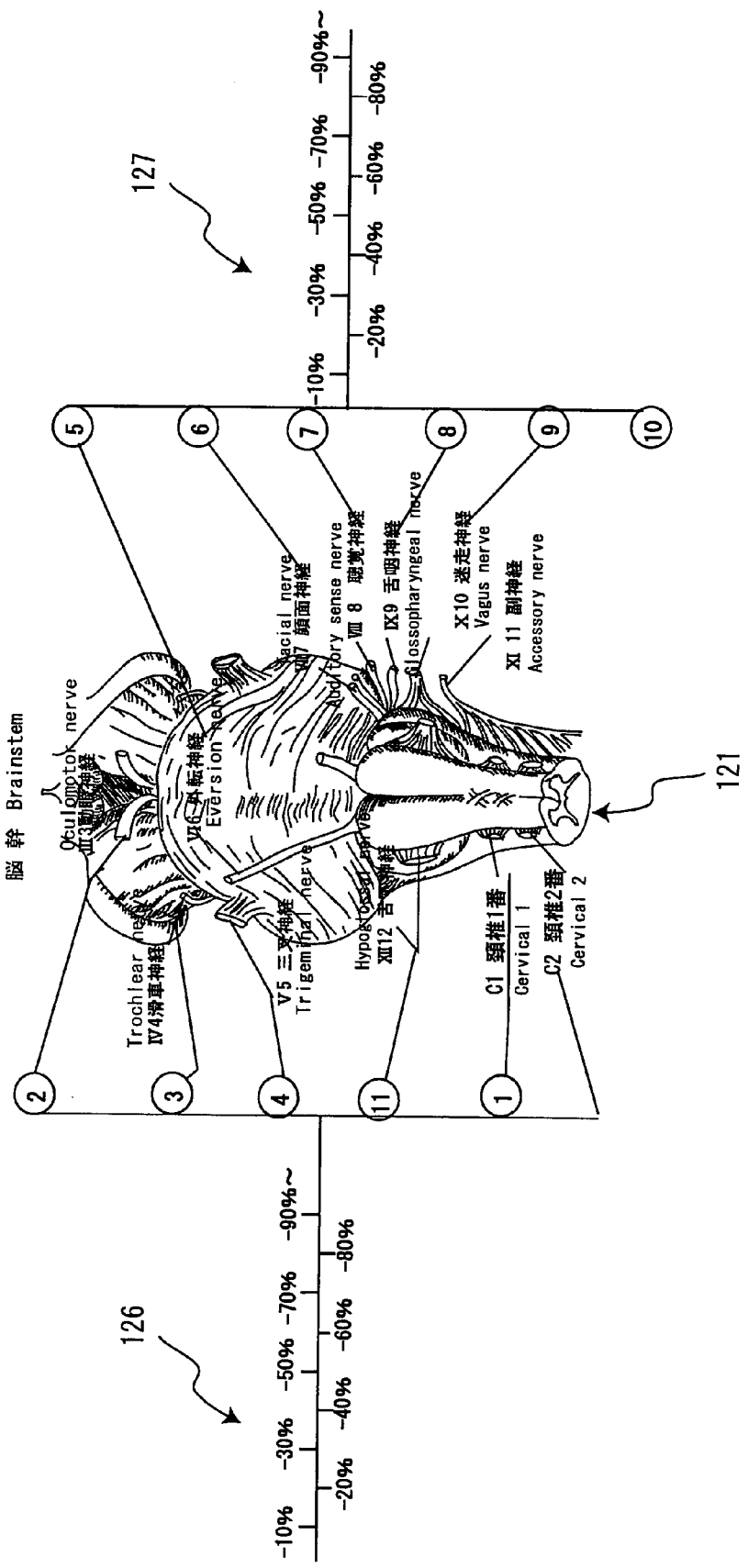

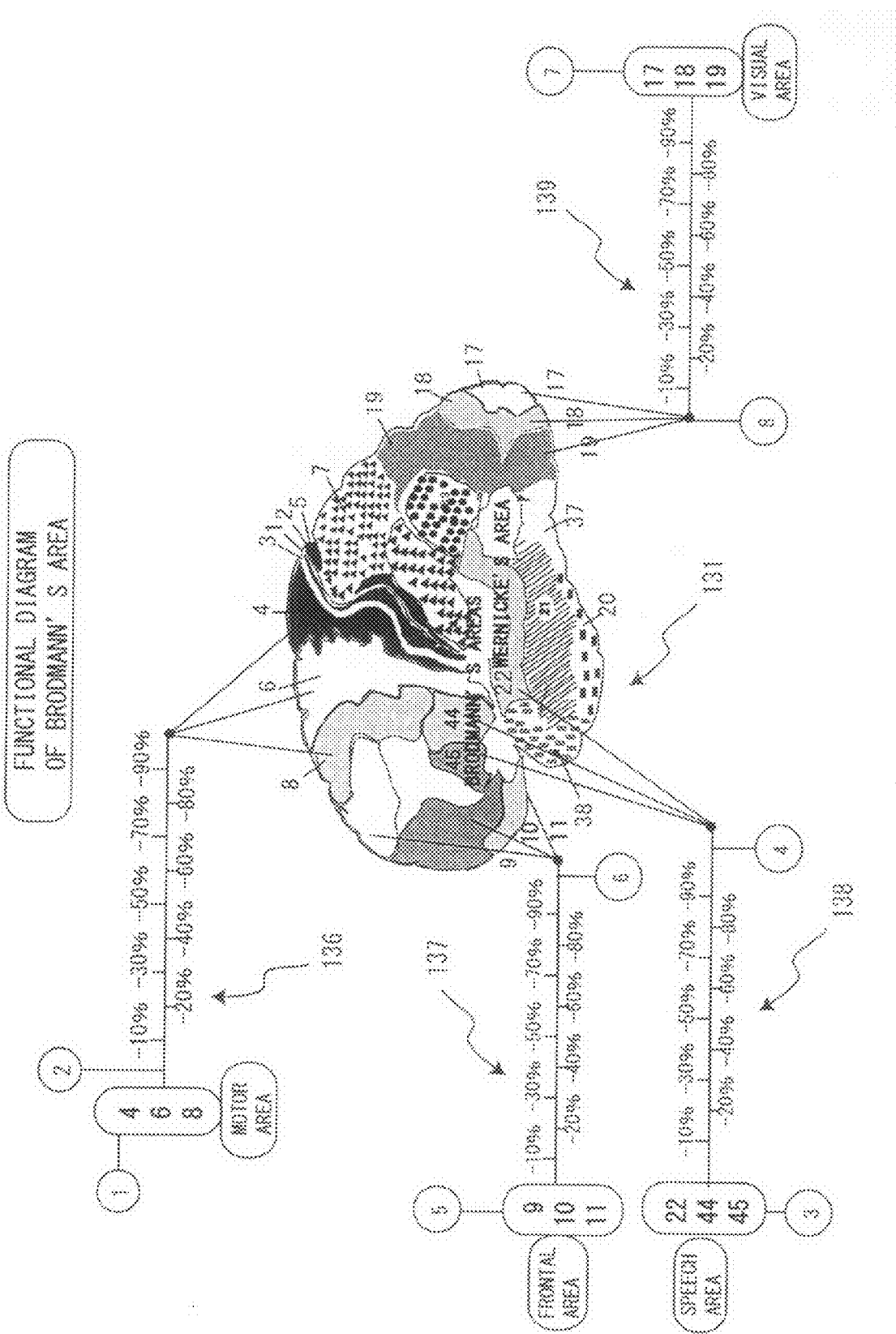

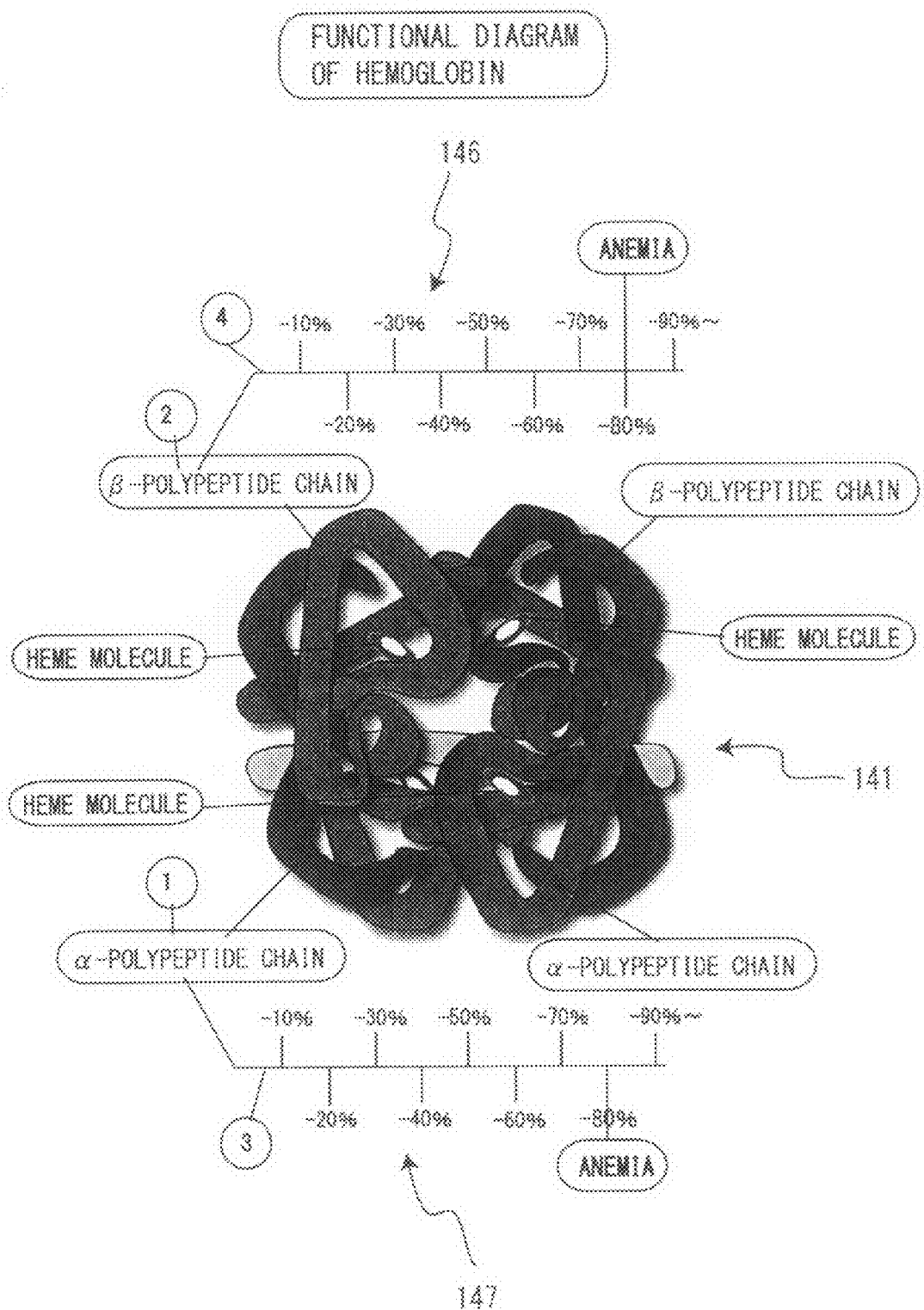

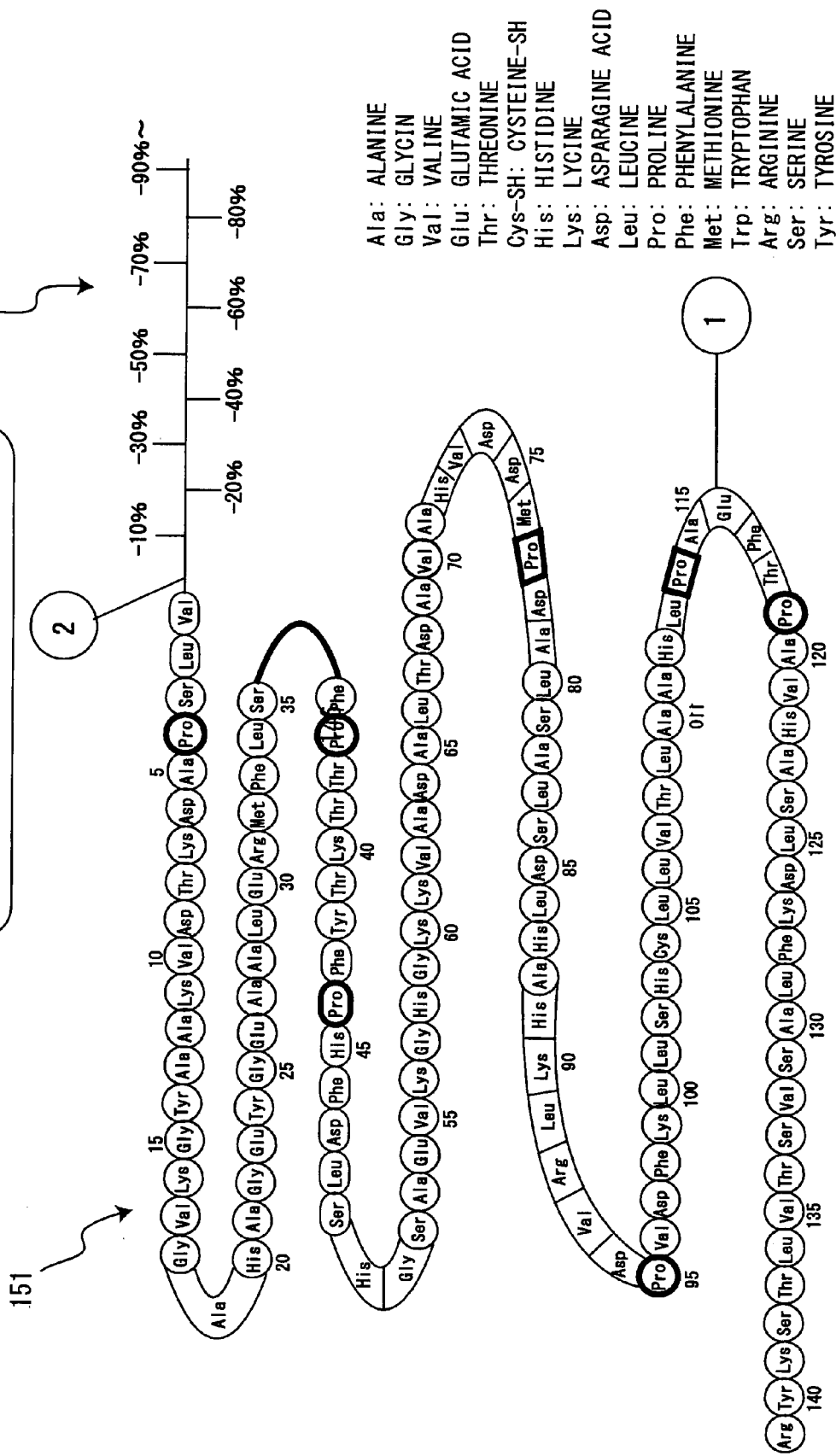
FIG. 15 FUNCTIONAL DIAGRAM OF AMINO ACID SEQUENCE OF ALPHA CHAIN

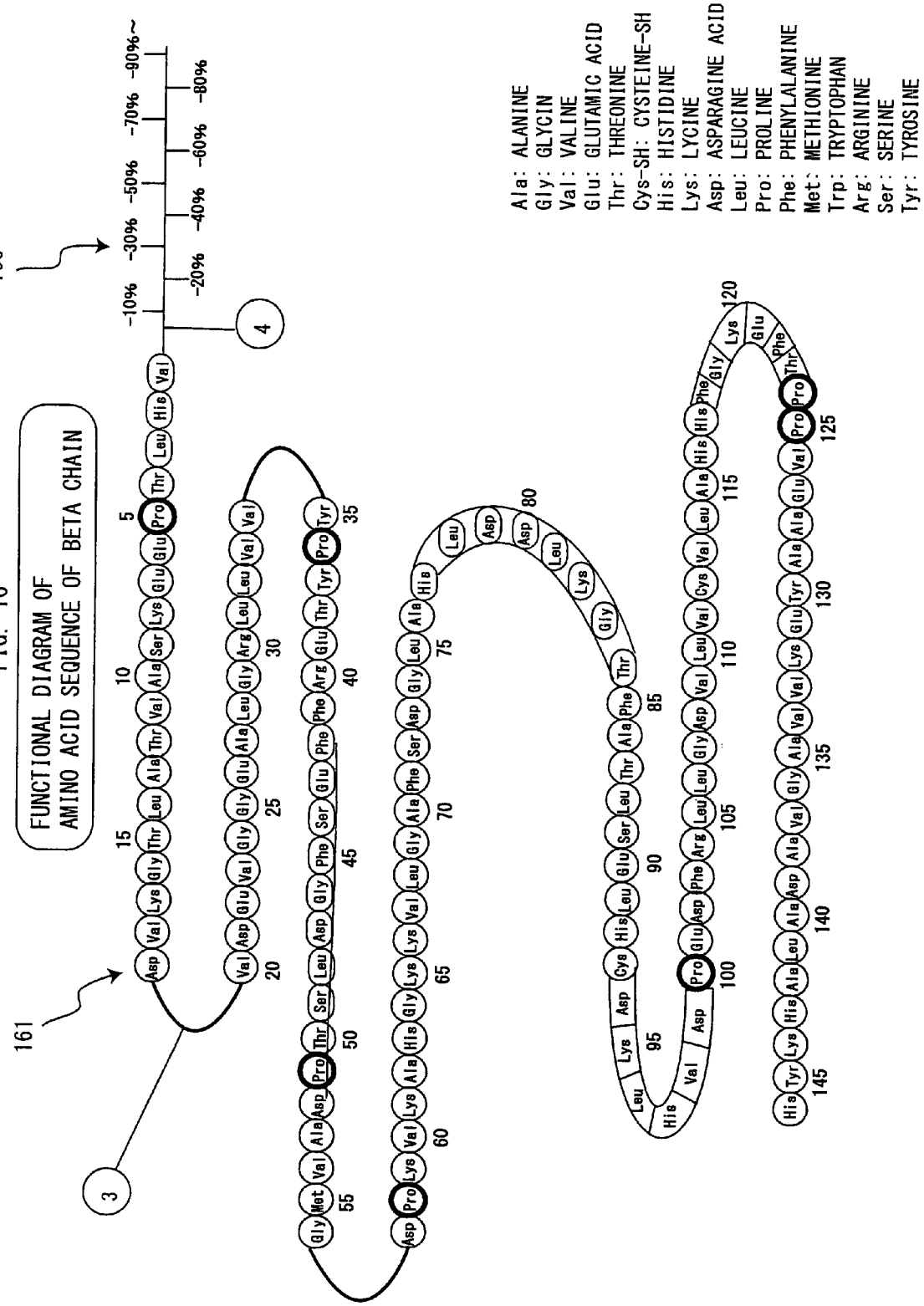

FIG. 17

MUSCLE REFLEX TREATMENT POINTS FOR SIX POINTS OF CEREBRUM

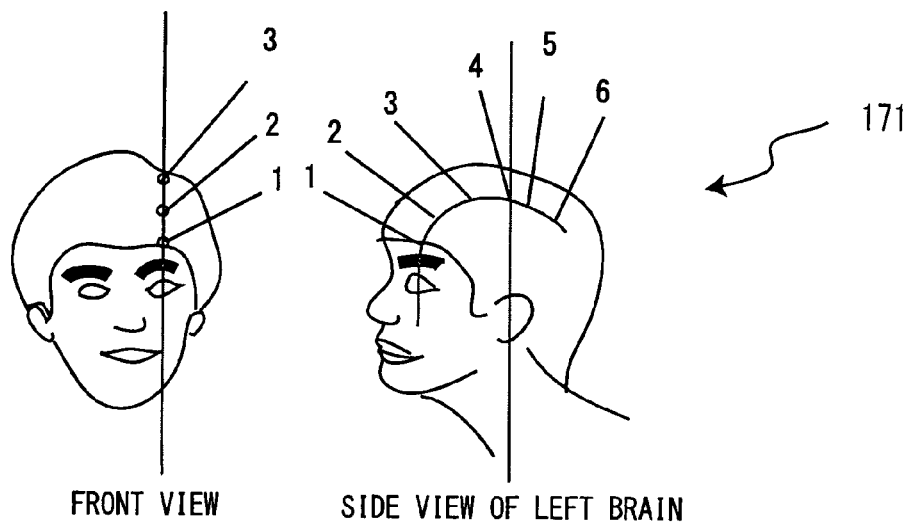

FRONT VIEW    SIDE VIEW OF LEFT BRAIN

To use this functional diagram, the muscle reflex test is performed at points 1 to 6 to determine a point where the functionality has declined, and then, the point is treated by stimulations.
Subsequently, the muscle reflex test is performed again to find whether powers of resistance have been obtained.

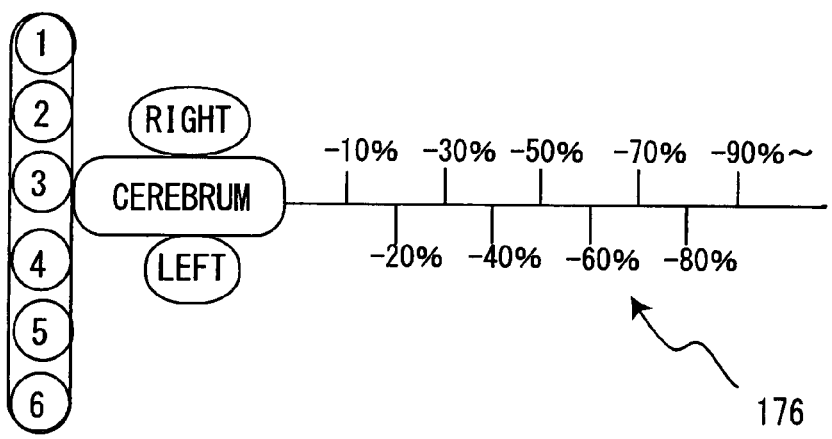

FUNCTIONAL DIAGRAM OF CONJUGATE GAZE MOTION OF EYES

FIG. 24
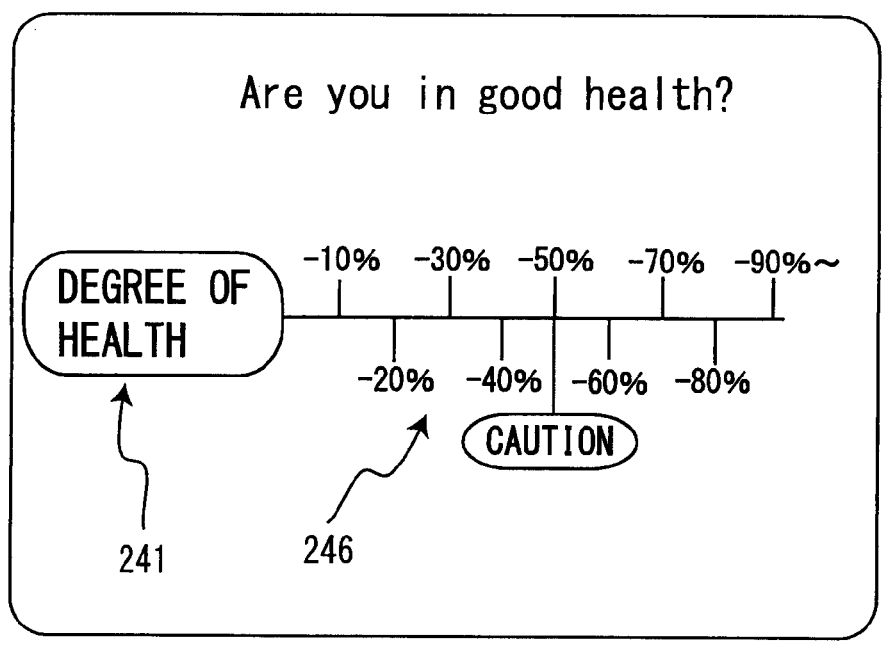
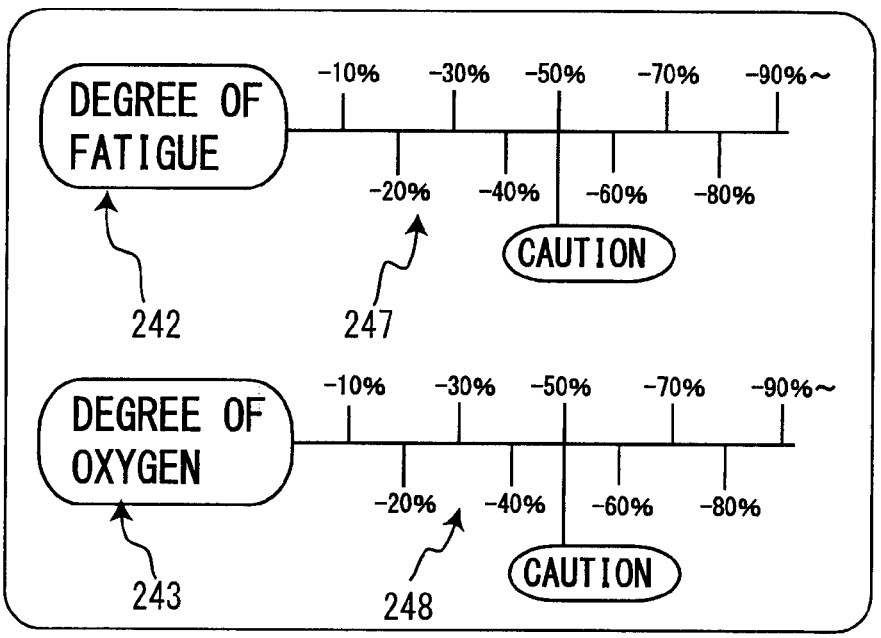

FIG. 25

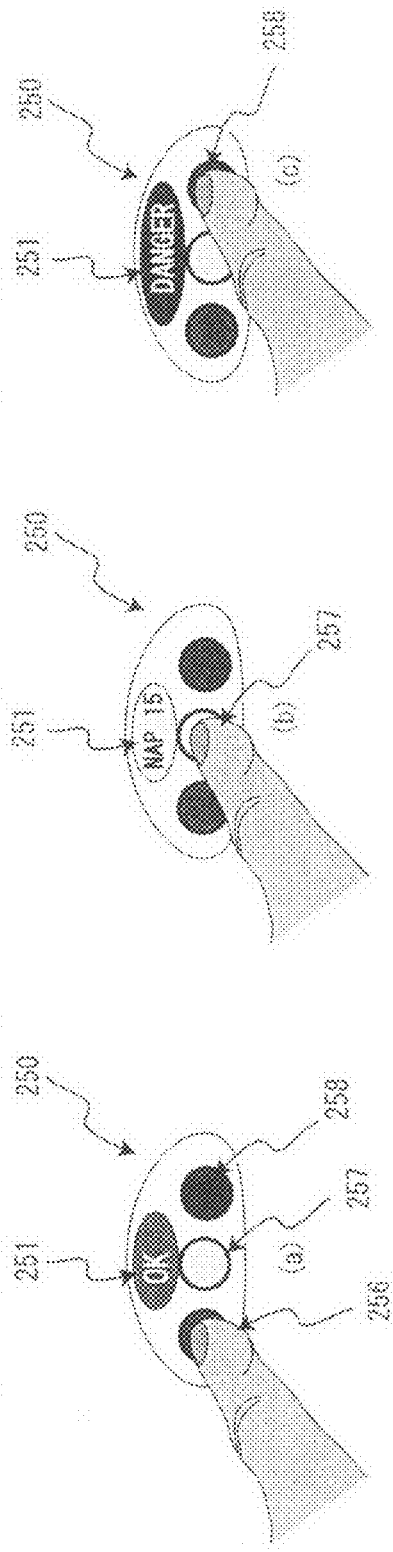

FATIGUE DISPLAY DEVICE

The fatigue display device displays with letters the degree of the absorbing of oxygen into brain cells.

O K······ The patient is normal and his or her degree of fatigue is 50% or less.

NAP 15 ····· The patient's degree of fatigue is 51% to 85%, and he or she need to take a nap for 15 minutes or more.

DANGER ····· The patient's degree of fatigue is 86% or more, and substantial sleep is required. (The patient may have symptoms such as yawns, concentration problems, and feeling sleepy.)

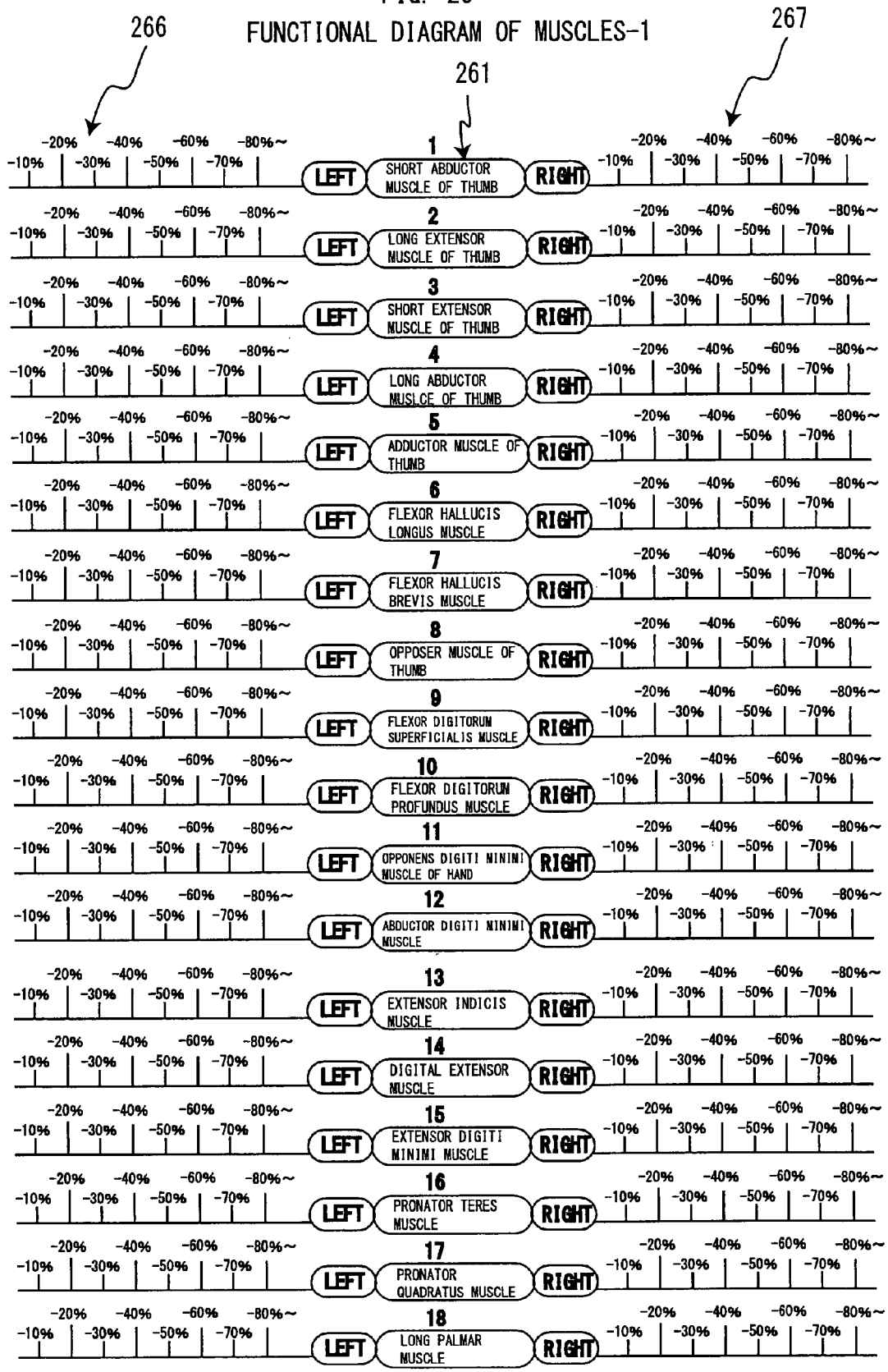
FIG. 26 FUNCTIONAL DIAGRAM OF MUSCLES-1

FUNCTIONAL DIAGRAM OF MUSCLES-2

FIG. 28 FUNCTIONAL DIAGRAM OF MUSCLES-3

FUNCTIONAL DIAGRAM FOR CELLULAR PHONE-1

FUNCTIONAL DIAGRAM FOR CELLULAR PHONE-2

FIG. 33 FUNCTIONAL DIAGRAM OF SHOULDER MUSCLES

FUNCTIONAL DIAGRAM OF VERTEBRAL ARTERY AT THE BASE OF BRAIN

FIG. 43
BLANK FUNCTIONAL DIAGRAM TO BE FILLED IN
FOR SIMPLE EXAMINATION
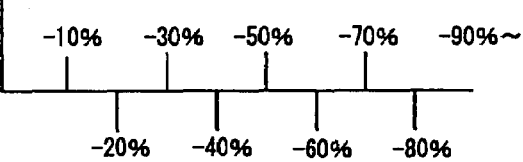
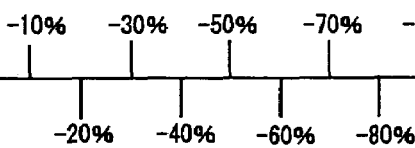

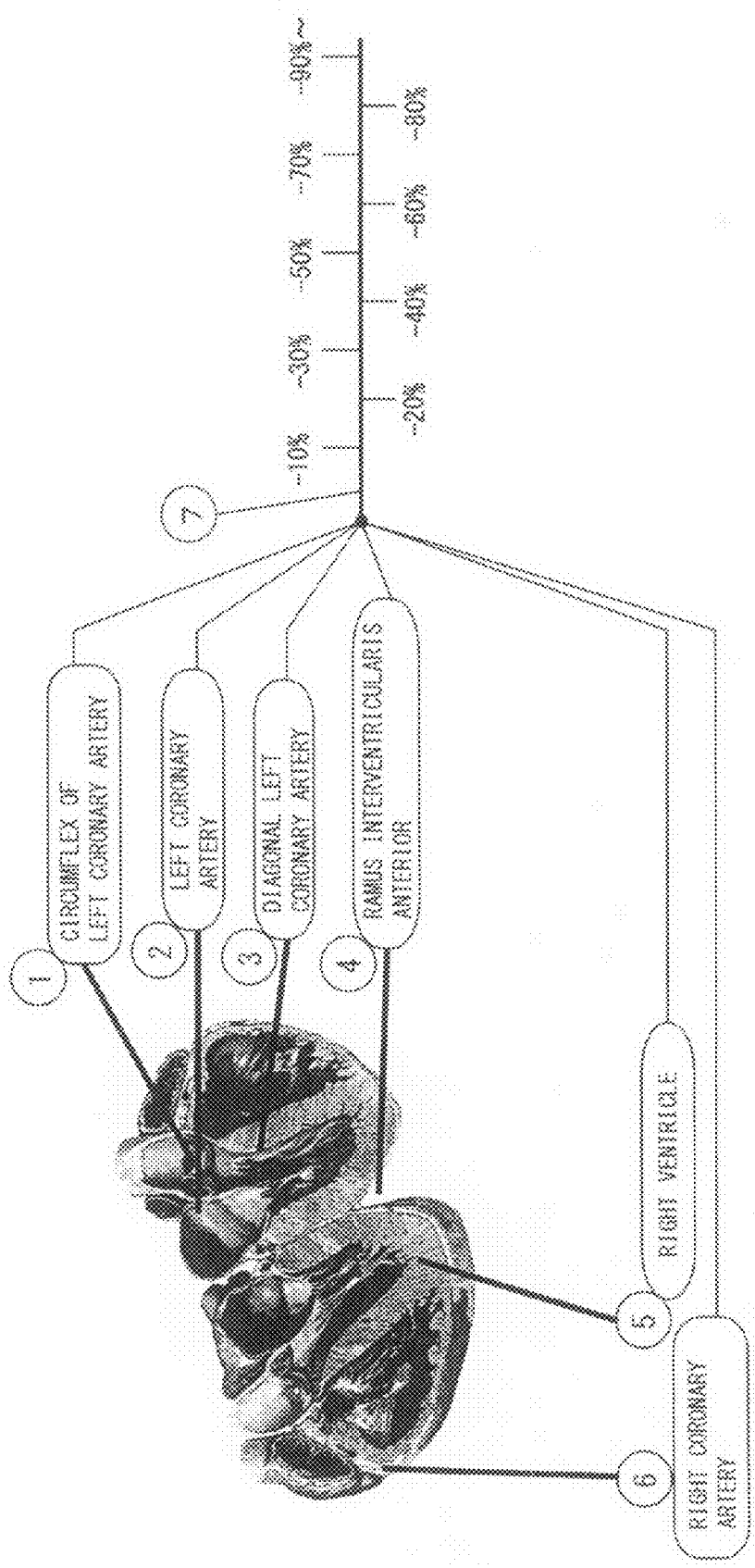

FUNCTIONAL DIAGRAM FOR MUSCLE AND MUSCLE STRENGTH REFLEX TEST AND EXAMINATION METHOD USING THE SAME

BACKGROUND OF THE INVENTION

1. Field of the Invention

This invention relates to a functional diagram suitably used for a muscle and muscle strength reflex test conducted in treatments such as chiropractic and the like and an examination method using the functional diagram, and more particularly, a functional diagram for a muscle and muscle strength reflex test that enables locating a damaged portion of a patient with high accuracy and an examination method using the functional diagram.

2. Description of Related Art

In conventional treatments such as chiropractic and the like, a muscle and muscle strength reflex test may be performed to locate a damaged portion of a patient or diagnose the severity of the damage. This reflex test uses a response of a muscle or muscle strength of the patient caused by an external stimulation affecting the body or mentality of the patient. "Bi-digital O-ring test" (U.S. Pat. No. 5,188,107) is well known as the reflex test. In the Bi-digital O-ring test, a practitioner such as chiropractic practitioner and the like attempts to force apart an O-ring shape formed by a patient who places the fingertips of his thumb and index, middle, ring, or little finger together, and the practitioner examines an instantaneous loosening of the muscle of the fingers being forced apart at the time when a certain external stimulation is affecting the patient.

When performing such tests, the practitioner sometimes explains a distortion and unleveling of the body during an examination. However, in fact, a patient cannot quite realize the distortion and unleveling. A body distortion check sheet, as described in Japanese Unexamined Patent Application Publication No. 2005-261881 (hereinafter referred to as "Iwashige"), is known as a means to solve such a problem. To use this body distortion check sheet, a patient steps on a footprint of the check sheet, takes repeated high steps thereon with his eyes blindfolded, driving his thighs high and swinging his arms much, for approximately sixty times, and then removes his blindfold and sees which direction the toes of his feet are pointing to and which direction and how much he has moved, thus determining the degree of the distortion and unleveling of his body.

The Japanese Unexamined Patent Application Publication No. 2003-310576 (hereinafter referred to as "Kayo") discloses a method of examining the distortion of a patient's body. In this method, the patient moves each of the joints of his body within its movable range, and the movement of the joint is assessed to find a direction in which the joint can be easily moved and a direction in which it is difficult to move the joint, so that the distortion of the patient's body is discovered. Kayo further discloses a recording method including the steps of preparing a schematic diagram of human body describing each of the joints of the entire body when lying on the back and lying on the face, writing and recording the movement and movable direction of the joints at each of the joints on the schematic diagram using numerals, symbols, and figures, and writing and recording a physique in a static condition on the schematic diagram.

However, the check sheet of Iwashige does not improve the accuracy with which the chiropractor locates a damaged portion, but it merely has the patient himself understand the distortion of his body. On the other hand, the schematic diagram disclosed by Kayo requires to examine and record the movement of all of the joints of the patient and his physique in a static condition, and therefore, the schematic diagram cannot be immediately applied for a particular examination such as the muscle reflex test and the muscle strength reflex test.

SUMMARY OF THE INVENTION

It is an object of the invention to provide a functional diagram for a muscle and muscle strength reflex test that enables a practitioner to locate a damaged portion of a patient with high accuracy when the practitioner performs the muscle and muscle strength reflex test.

In accordance with an aspect of the present invention, a muscle and muscle strength reflex test includes an image portion identifying a prescribed examination item and a scale portion arranged adjacent to the image portion and having a scale representing a degree of the examination item.

Furthermore, the scale may have a plurality of discrete numbers lined up therewith.

Furthermore, a patient may touch a portion of the scale to undergo a first muscle and muscle strength reflex test, and then, the patient may touch a different portion of the scale depending on a result of the first muscle and muscle strength reflex test to undergo a second muscle and muscle strength reflex test.

Furthermore, the image portion and the scale portion may be printed on a printed matter or may be displayed on a monitor display of an electronic device.

In accordance with another aspect of the present invention, an examination method for examining a patient with the use of a functional diagram for a muscle and muscle strength reflex test includes the steps of having a patient touch a portion of the functional diagram representing a portion or symptom of his body with one of his fingers of one of his hands and having a patient undergo the muscle and muscle strength reflex test to examine the portion or symptom of his body represented by the portion of the functional diagram touched by the patient.

Furthermore, the functional diagram may have an image portion representing the portion or symptom of his body and a scale portion arranged adjacent to the image portion and having a scale representing a degree of a damage of the portion or symptom.

Furthermore, the muscle and muscle strength reflex test may include the steps of having the patient form an O-Ring shape with the other of his hands by placing the fingertips of his thumb and one of his remaining fingers together and attempting to pull apart the O-Ring shape to measure a muscle strength of the fingers.

Furthermore, the patient may touch a plurality of portions of the functional diagram, one by one, and the muscle and muscle strength reflex test is performed to determine a muscle strength at each of the plurality of the portions, so that the muscle strength at each of the plurality of the portions can be compared with each other.

BRIEF DESCRIPTION OF THE DRAWINGS

The above and other objects and features of the invention are apparent to those skilled in the art from the following preferred embodiments thereof when considered in conjunction with the accompanied drawings, in which:

FIG. 2 is a perspective view showing a functional diagram of ankle fatigue;

FIG. 3 is a perspective view showing a functional diagram of pelvic unleveling and functional decline rate;

FIG. 4 is a perspective view showing a functional diagram of sciatic nerve and femoral nerve;

FIG. 5 is a perspective view showing a functional diagram of major psoas muscle;

FIG. 6 is a perspective view showing a functional diagram of gluteus maximus muscle;

FIG. 7 is a perspective view showing a functional diagram of lumbar spine and sacral spine;

FIG. 8 is a perspective view showing a functional diagram of cervical vertebra;

FIG. 9 is a perspective view showing a functional diagram of cerebellar hypofunction;

FIG. 10 is a perspective view showing a functional diagram of vertebral artery and C1 to C3;

FIG. 11 is a perspective view showing a functional diagram of vertebral artery;

FIG. 12 is a perspective view showing a functional diagram of brainstem (cranial nerve);

FIG. 13 is a perspective view showing a functional diagram of brodmann's area;

FIG. 14 is a perspective view showing a functional diagram of hemoglobin;

FIG. 15 is a perspective view showing a functional diagram of amino acid sequence of alpha chain;

FIG. 16 is a perspective view showing a functional diagram of amino acid sequence of beta chain;

FIG. 17 is a perspective view showing a functional diagram of six points of cerebrum;

FIG. 24 is a perspective view showing a functional diagram for simple health checkup;

FIG. 25 is a perspective view showing a functional diagram of the fatigue display device;

FIG. 26 to FIG. 29 are perspective views showing functional diagrams of muscles 1 to 4;

FIG. 43 is a perspective view showing a blank functional diagram for a simple examination; and FIG. 44 is a perspective view showing a functional diagram of coronary artery of heart.

DETAILED DESCRIPTION OF THE PREFERRED EMBODIMENTS

Figure 1:
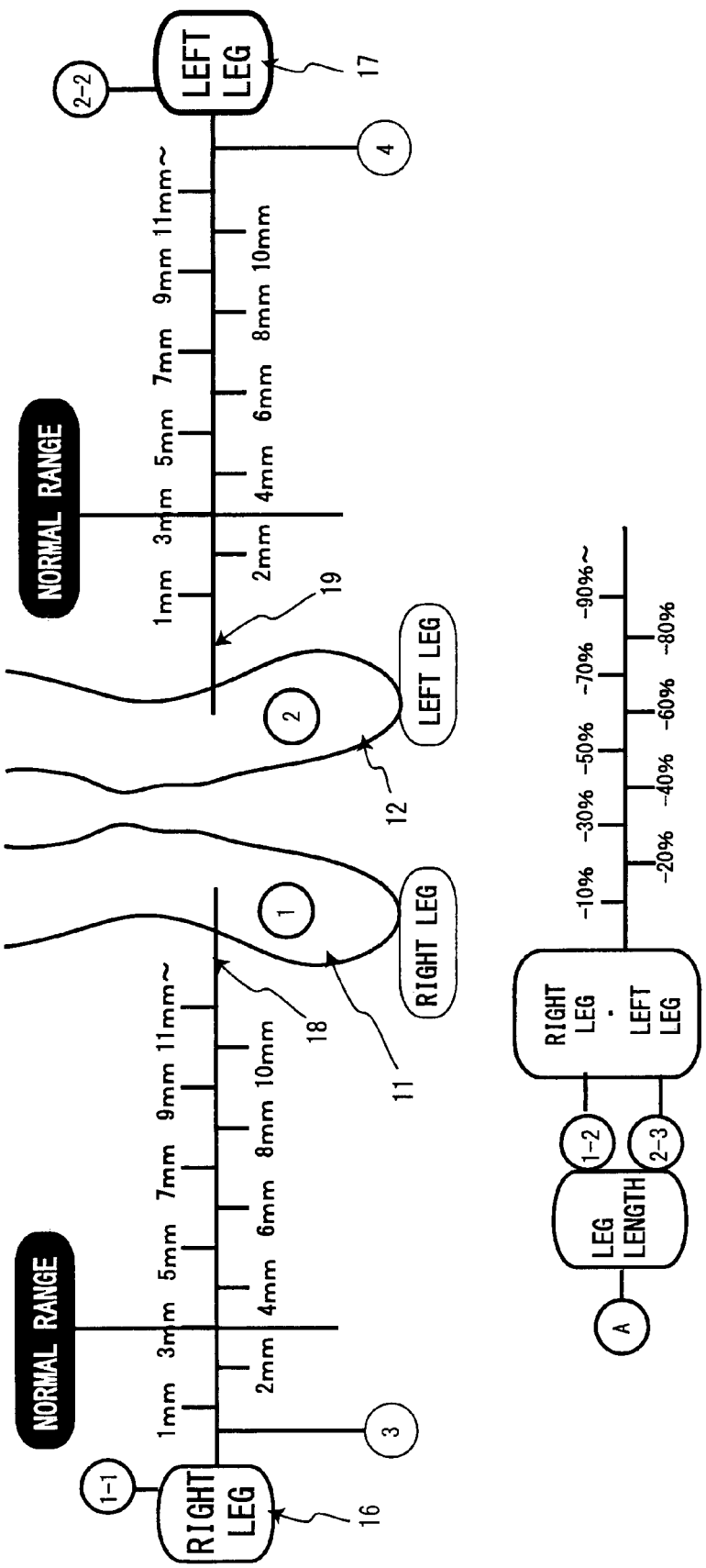
FIG. 1 is a perspective view showing a functional diagram of leg length.

FIG. 1 is an example of the functional diagram for muscle and muscle strength reflex test of the present invention, and is a functional diagram of leg length. The functional diagram of the leg length is used to determine which leg is shorter in a case where there is a difference of length between the right and left legs. In FIG. 1, an image portion is an illustration showing a right leg 11 and a left leg 12, and scale portions 16 and 17 respectively have graduation portions 18 and 19.

The functional diagram is used to diagnose a patient during treatments. A patient is asked to form an O shape by placing the fingertips of his thumb and index finger together, and the practitioner detects the muscle strength of the fingers forming the O shape. Subsequently, the patient forms O shapes by placing the fingertips of his thumb and middle, ring, and little fingers, one by one, and the practitioner detects the muscle strength of the respective O shapes formed by the patient. The practitioner detects the muscle strength by applying force in a direction to spread apart the O shapes formed by the fingers of the patient. While the practitioner detects the muscle strength as described above, the patient touches a portion of the functional diagram and touches different portions thereof as needed. Where the patient touches an image portion of the functional diagram representing a portion of his body that is damaged and abnormal, the muscle strength is detected to be weaker. Where the patient touches an image portion of the functional diagram representing a portion of his body that is healthy and normal, the muscle strength is detected to be stronger. Where the patient touches a scale portion of the functional diagram representing an incorrect degree, the muscle strength is detected to be weaker. Where the patient touches a scale portion of the functional diagram representing a correct degree, the muscle strength is detected to be stronger. These steps are repeated to determine a damaged portion of the patient and the degree of the damage.

The functional diagram can also be used with other detection methods such as knee-lowering muscle test, arm-pull-down muscle test, and upper body inclining muscle test. In the knee-lowering muscle test, the patient sits down, touches a portion of the functional diagram of the present invention with, for example, his left index finger, and slightly lifts his right knee, and the practitioner applies downward force with his hand to the lifted knee of the patient to examine the muscle strength of the patient. In the arm-pull-down muscle test, the patient touches a portion of the functional diagram of the present invention and extends his arm horizontally, and the practitioner applies force to the horizontally-extended arm of the patient to examine the muscle strength. In the upper body inclining muscle test, the patient touches a portion of the functional diagram and inclines his upper body toward the practitioner, and the practitioner pushes back the patient to examine the muscle strength of the patient. Each of the above muscle and muscle strength reflex tests is suitably used with all of the functional diagrams as described below.

FIG. 2 is an example of the functional diagram for muscle and muscle strength reflex test of the present invention and is a functional diagram of ankle fatigue. The functional diagram of this example indicates the degree of fatigue of each of the right and left ankles by percentage, and is used to examine whether the damaged portion is on the inner or outer side and what percentage of the functionality of the right or left leg is declined. The functional diagram has image portions 21 and 22 and scale portions 26 and 27 arranged adjacent to the image portions 21 and 22. This functional diagram is used for the above-described muscle and muscle strength reflex tests and improves the accuracy of the examination.

FIG. 3 is an example of the functional diagram for muscle and muscle strength reflex test of the present invention and is a functional diagram of pelvic unleveling and functional decline rate. The functional diagram for pelvic unleveling and functional decline rate is used to examine how the pelvis is deformed, whether the right rear or left rear is inclined downward, whether the deformation is inward or outward, and what percentage of the functionality is declined. An image portion 31 describing a pelvis is formed at a substantial center of the diagram, and an image portion 32 arranged below the image portion 31 has six illustrations of pelvises each showing a point of the pelvis. Scale portions 36 and 37 are arranged on either side of the image portion 31, and each scale in the scale portions 36 and 37 corresponds to a respective point of the pelvis.

FIG. 4 is an example of the functional diagram for muscle and muscle strength reflex test of the present invention and is a functional diagram of sciatic nerve and femoral nerve. The functional diagram of sciatic nerve and femoral nerve is used to examine which side of the sciatic nerve, the tibial nerve, and the common peroneal nerve are damaged, what percentage is the degree of the damages, what percentage is the degree of a damage of the femur, which of the right or left side is damaged, and what percentage of the functionality is declined. An image portion 41 in a shape of an arrow is formed at a substantial center of the diagram, and a scale portion 46 for femoral nerve, a scale portion 49 for sciatic nerve, a scale portion 48 for tibial nerve, and a scale portion 47 for common peroneal nerve are formed around the image portion 41.

FIG. 5 is an example of the functional diagram for muscle and muscle strength reflex test of the present invention and is a functional diagram of major psoas muscle. The functional diagram of major psoas muscle is used to examine whether the major psoas muscle and the major psoas muscle nerves are damaged, which of the right or left side is damaged, what percentage of the functionality is declined, and the like. An image portion 51 of the major psoas muscle is formed at the upper right in the functional diagram, and a scale portion 56 of the major psoas muscle is formed lateral to the image portion 51. An image portion 52 of the major psoas muscle nerves is formed at the lower left of the diagram, and a scale portion 57 of the major psoas muscle nerves is formed lateral to the image portion 52.

FIG. 6 is an example of the functional diagram for muscle and muscle strength reflex test of the present invention and is a functional diagram of gluteus maximus muscle. The functional diagram of gluteus maximus muscle is used to examine whether the gluteus maximus muscle is damaged, which of the right or left side is damaged, to what degree the functionality is declined, and whether the functionality of the exiting portion of the nerves controlling the gluteus maximus muscle is declined. In the same manner as the diagram of FIG. 5, an image portion 61 of the gluteus maximus muscle is formed at the upper left, and a scale portion 66 is formed lateral to the image portion. An image portion 62 of the gluteus maximus muscle nerves is formed at the lower right, and a scale portion 67 of the gluteus maximus muscle nerves is formed lateral to the image portion 62.

FIG. 7 is an example of the functional diagram for muscle and muscle strength reflex test of the present invention and is a functional diagram of lumbar spine and sacral spine. The functional diagram of lumbar spine and sacral spine detects whether the lumbar spine is damaged, which vertebra is damaged, whether the damage is on the right or left side, what percentage of the functionality is declined, and subsequently, whether the sacral spine is damaged, which vertebra is damaged, what percentage of the functionality is declined. An image portion 71 of lumbar spine and sacral spine is arranged at a substantial center of the diagram, and a scale portion 76 of lumbar spine and a scale portion 77 of sacral spine are arranged in the diagram.

FIG. 8 is an example of the functional diagram for muscle and muscle strength reflex test of the present invention and is a functional diagram of cervical vertebra. The functional diagram of cervical vertebra is used to examine whether the cervical vertebrae are damaged and whether the damage is on the right or left side. Subsequently, the damage and the decline rate of functionality are examined from the first cervical vertebra to the first thoracic vertebra. An image portion 81 in a shape of a cervical vertebrae is formed at a substantial center of the diagram, and a scale portion 86 and a scale portion 87 are arranged on either side of the image portion 81.

FIG. 9 is an example of the functional diagram for muscle and muscle strength reflex test of the present invention and is a check diagram of cerebellar hypofunction. The check diagram of cerebellar hypofunction is used to examine the damage of the cerebellum and whether the damage is on the left or right side. Subsequently, the decline rate of the functionality of the cerebellum is examined. An image portion 91 in a shape of a cerebellum is described at an approximate center of the diagram, and a scale portion 96 and a scale portion 97 for examining whether the damage is at the left or right side are arranged on either side of the image portion 91. A scale portion 98 for examining the decline rate of the functionality of the cerebrum is also arranged in the diagram.

FIG. 10 is an example of the functional diagram for muscle and muscle strength reflex test of the present invention and is a functional diagram of vertebral artery and C1 to C3. It is generally not easy to confirm compression stenosis of the vertebral artery, but the compression stenosis can be identified by a shift of the cervical vertebrae. Whether the damage is on the right or left side is determined by a rotation of the first cervical vertebra. Subsequently, the decline rate of the functionality, namely, the degree of the compression, is examined. An image portion 101 is arranged to describe the arterial system from basilar artery to vertebral artery and aorta, and a scale portion 106 is arranged at the left of the image portion 101 to correspond to each point of the artery.

FIG. 11 an example of the functional diagram for muscle and muscle strength reflex test of the present invention and is another functional diagram of vertebral artery. FIG. 11 is the same as FIG. 10 in that the diagram of FIG. 11 is also used to examine functions related to the vertebral artery, but a picture taken by MR (Magneto Resonance) is used in an image portion 111 and an image portion 112 in FIG. 11. A scale portion 116 and a scale portion 117 are arranged on either side of the image portion 111 and the image portion 112.

FIG. 12 is an example of the functional diagram for muscle and muscle strength reflex test of the present invention and is a functional diagram of brainstem (cranial nerve). This functional diagram of brainstem (cranial nerve) is used to examine functions of cranial nerves originating from a brainstem, and more specifically, ten nerves originating from the brainstem among twelve cranial nerves, namely, third cranial nerve (oculomotor nerve), fourth cranial nerve (trochlear nerve), fifth cranial nerve (trigeminal nerve), sixth cranial nerve (abducent nerve), seventh cranial nerve (facial nerve), eighth cranial nerve (vestibulocochlear nerve), ninth cranial nerve (glossopharyngeal nerve), tenth cranial nerve (vagus nerve), eleventh cranial nerve (accessory nerve), and twelfth cranial nerve (hypoglossal nerve). In addition, the first cervical vertebra and the second cervical vertebra can be examined. An image portion 121 In a shape of a brainstem is described at a substantial center of the diagram, and a scale portion 126 and a scale portion 127 for examining whether the damage is on the left or right side are arranged on either side of the image portion 121.

FIG. 13 is an example of the functional diagram for muscle and muscle strength reflex test of the present invention and is a functional diagram of brodmann's area. The functional diagram of brodmann's area is used to examine the degree of functional decline of the cortex on the surface of the cerebrum, and the examination is performed using the diagram having reference signs each corresponding to the major portions. Motor area (4, 6, and 8), frontal area (9, 10, and 11), visual area (17, 18, and 19), speech area (22, 44, and 45), and the like are examined to determine a damaged portion and measure a decline rate of the functionality. A image portion 131 is described in a shape of a brain is described in a substantial center, and scale portions 136 to 139 for examining whether the damage is in the motor area, frontal area, visual area, or the speech area are arranged around the image portion 131.

FIG. 14 is an example of the functional diagram for muscle and muscle strength reflex test of the present invention and is a functional diagram of hemoglobin. The functional diagram of hemoglobin is used to examine the degree of coupling of oxygen and the decline ratio of the functionality of alpha and beta polypeptide chains. Symptoms of anemia can be known from the result of this examination. An image portion 141 in a shape of hemoglobin is arranged at a substantial center of the diagram, and a scale portion 146 and a scale portion 147 are arranged around the image portion 141 and are used to examine whether the alpha and beta polypeptide chains are damaged.

FIG. 15 and FIG. 16 are examples of the functional diagram for muscle and muscle strength reflex test of the present invention and are functional diagrams of amino acid sequence of alpha chain and beta chain, respectively. The functional diagrams of amino acid sequence of alpha chain and beta chain are used to help the practitioner detect amino acids hindering the coupling of oxygen. An image portion 151 and an image portion 161 respectively representing amino acid sequences of alpha chain and beta chain are arranged in a substantial center of the diagram, and a scale portion 156 and a scale portion 166 are described at the upper right corner.

FIG. 17 is an example of the functional diagram for muscle and muscle strength reflex test of the present invention and is a functional diagram of six points of cerebrum. The functional diagram of six points of cerebrum is used to determine which portion in the motor area of the cerebrum should be give a stimulation to redress the balance of functionality, and is used to treat the determined portion. To use the functional diagram, the muscle reflex test is performed at points 1 to 6 to determine a point where the functionality has declined, and then, the point is treated by stimulations. Subsequently, the muscle reflex test is performed again to find whether powers of resistance have been obtained. An image portion 171 describing frontal and lateral view of a human head is arranged at a upper center of the diagram, and a scale portion 176 is arranged at a lower portion of the diagram.

Figure 18:
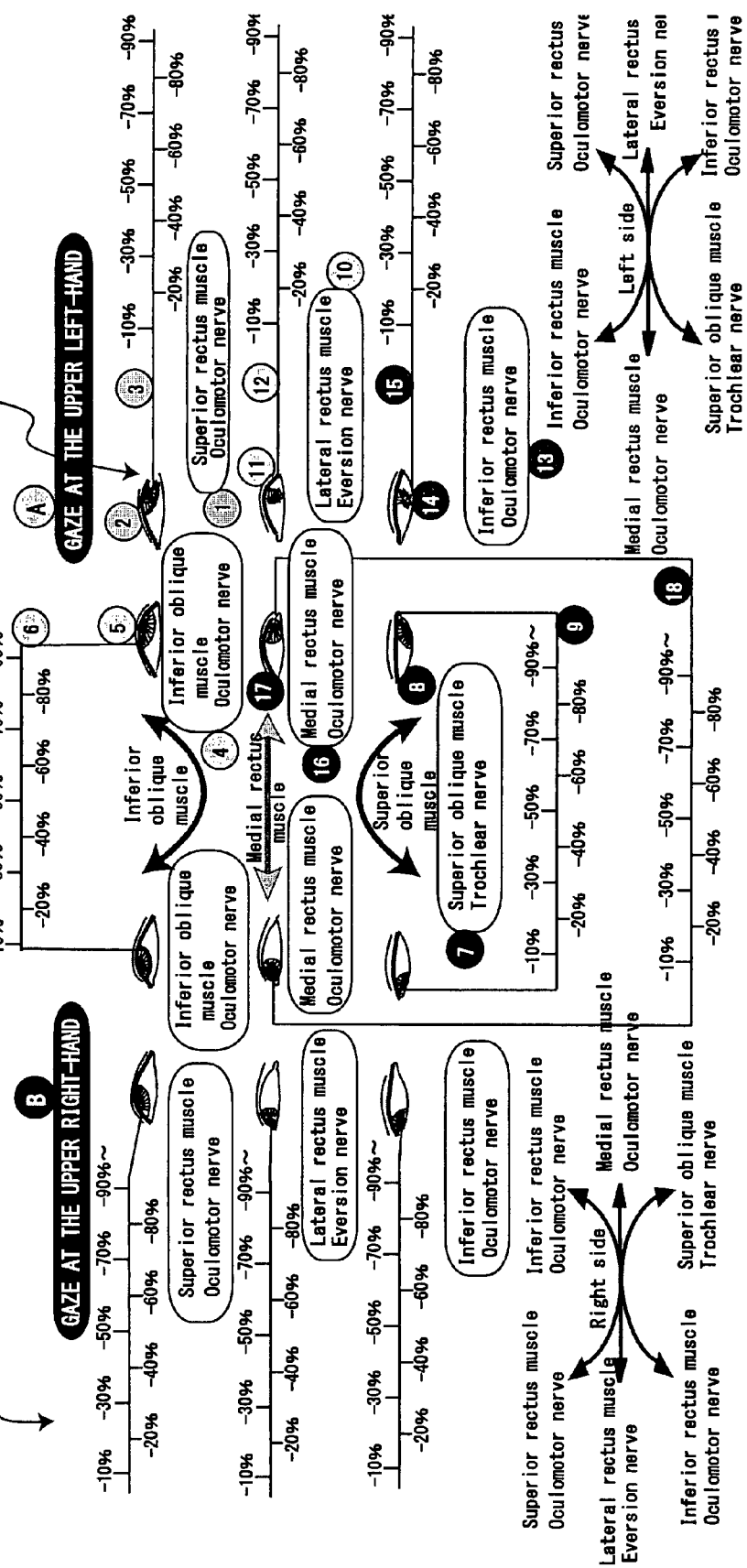
FIG. 18 is a perspective view showing a functional diagram of conjugate gaze motion of eyes.

FIG. 18 is an example of the functional diagram for muscle and muscle strength reflex test of the present invention and is a functional diagram of conjugate gaze motion of eyes. It is known that cranial nerve disorder decreases the ability of the movement of eyes, and this functional diagram is used to perform examinations based on such empirical rule. This functional diagram enables the practitioner to determine a damaged portion and the decline rate of the conjugate gaze motion through examination. An image portion 181 describing the movement of an eye is arranged at a substantial center of the diagram, and a scale portion 186 for examining whether the eye is damaged is arranged around the image portion 181.

Figure 19:
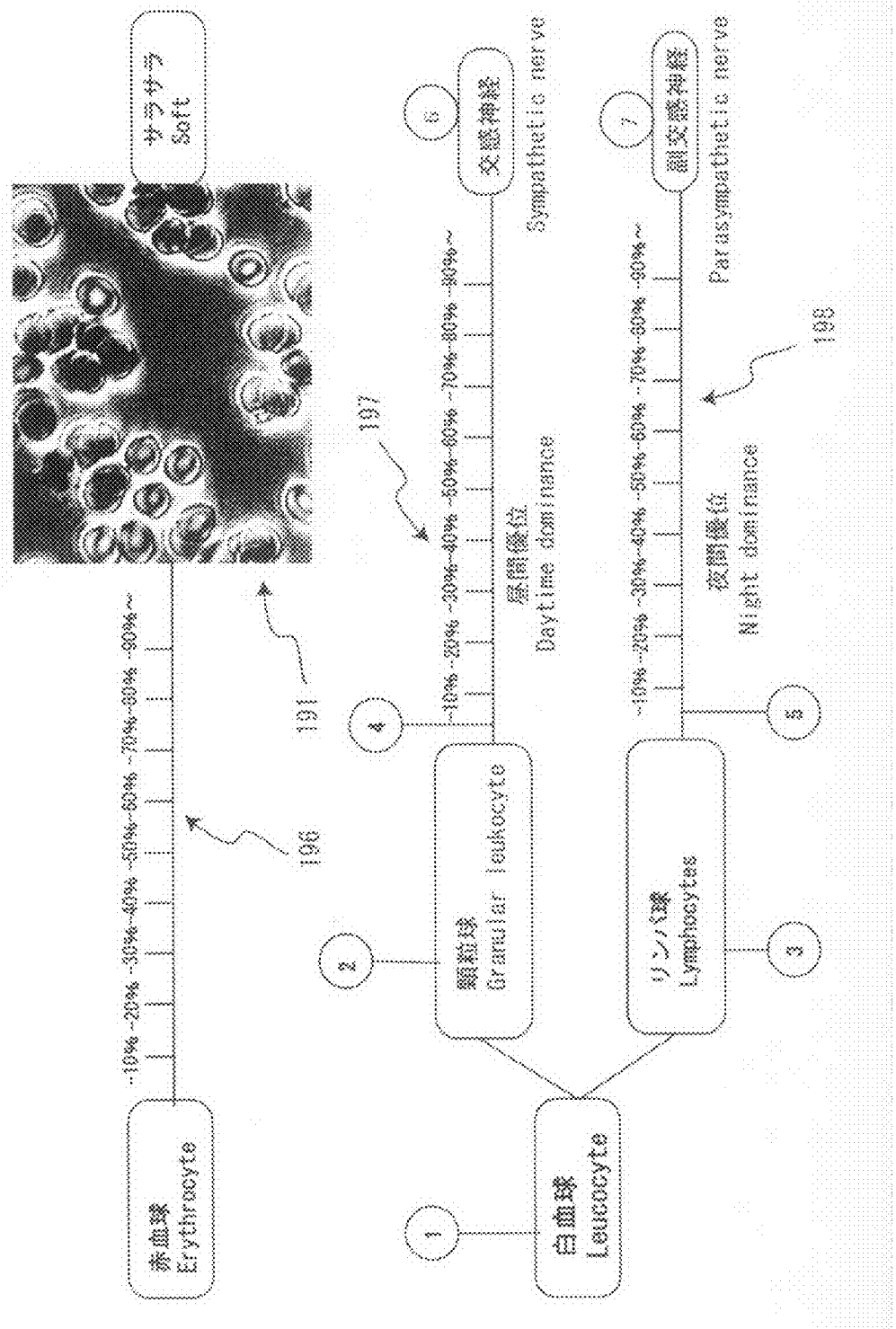
FIG. 19 is a perspective view showing a functional diagram of erythrocyte and leukocyte.

FIG. 19 is an example of the functional diagram for muscle and muscle strength reflex test of the present invention and is a functional diagram of erythrocyte and leukocyte. The status of erythrocyte and the condition of health of the body have correlation with each other, and the viscosity of the erythrocyte is preferred to be lower for a healthy body. An autonomic disorder may disrupt the balance of leukocyte, and thus, it is important to examine the functional decline of not only erythrocyte but also granular leukocyte and lymphocyte as leukocyte for the maintenance of good health. FIG. 19 has an image portion 191 including a macro photograph of blood and further has a scale portion 196 of erythrocyte, a scale portion 197 of granular leukocyte, and a scale portion 198 of lymphocyte around the image portion 191.

Figure 20:
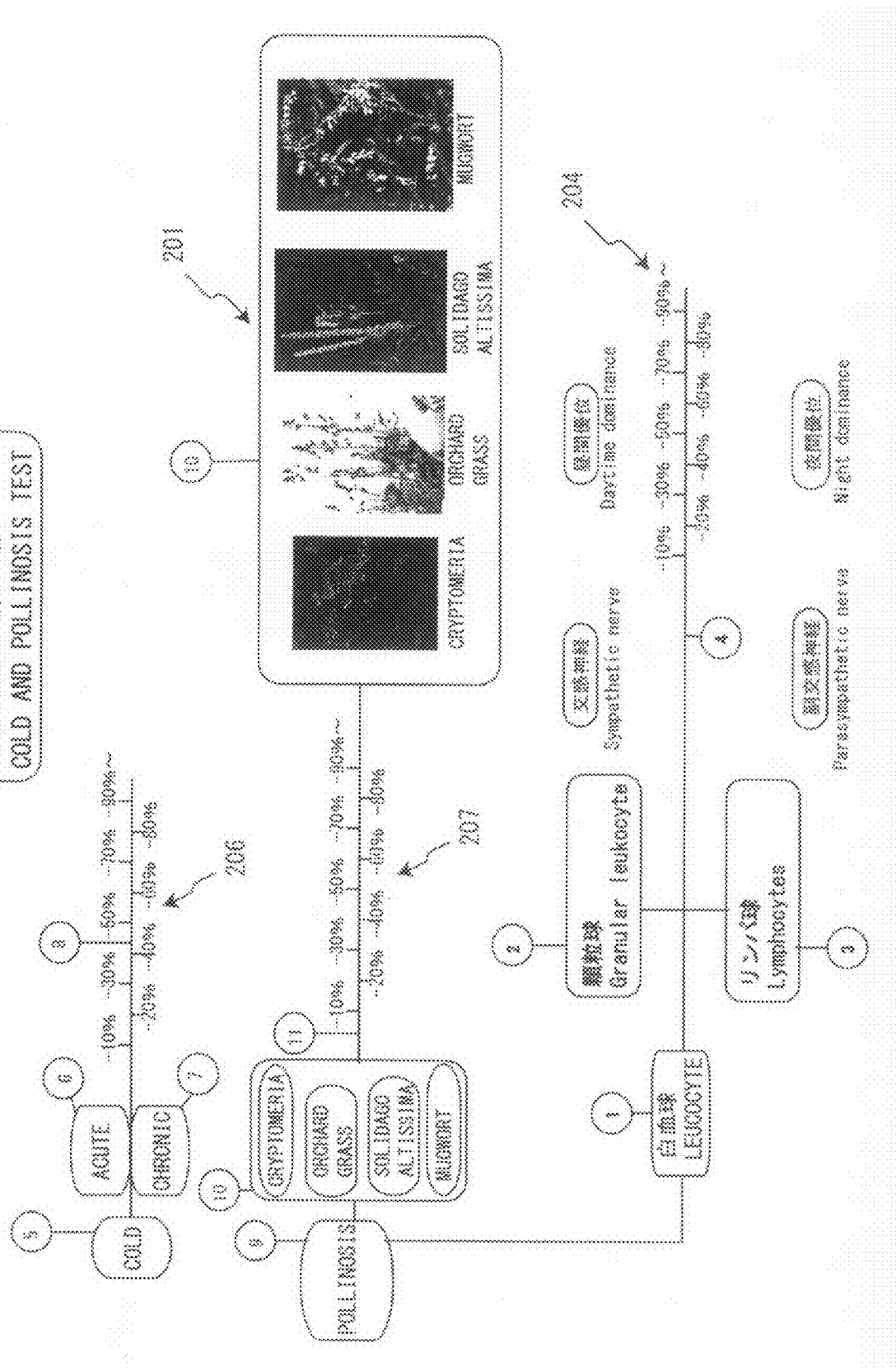
FIG. 20 is a perspective view showing a functional diagram of cold and pollinosis examination.

FIG. 20 is an example of the functional diagram for muscle and muscle strength reflex test of the present invention and is a functional diagram of cold and pollinosis examination. FIG. 20 has an image portion 204 for examining the functional decline of granular leukocyte and lymphocyte as leukocyte just as FIG. 19 for immunological test, and the image portion 204 is used to obtain a reference value in conjunction with the examination. FIG. 20 further has an image portion 201 including pictures of various plants causing the pollinosis, and has a scale portion 206 for cold and a scale portion 207 for the pollinosis.

Figure 21:
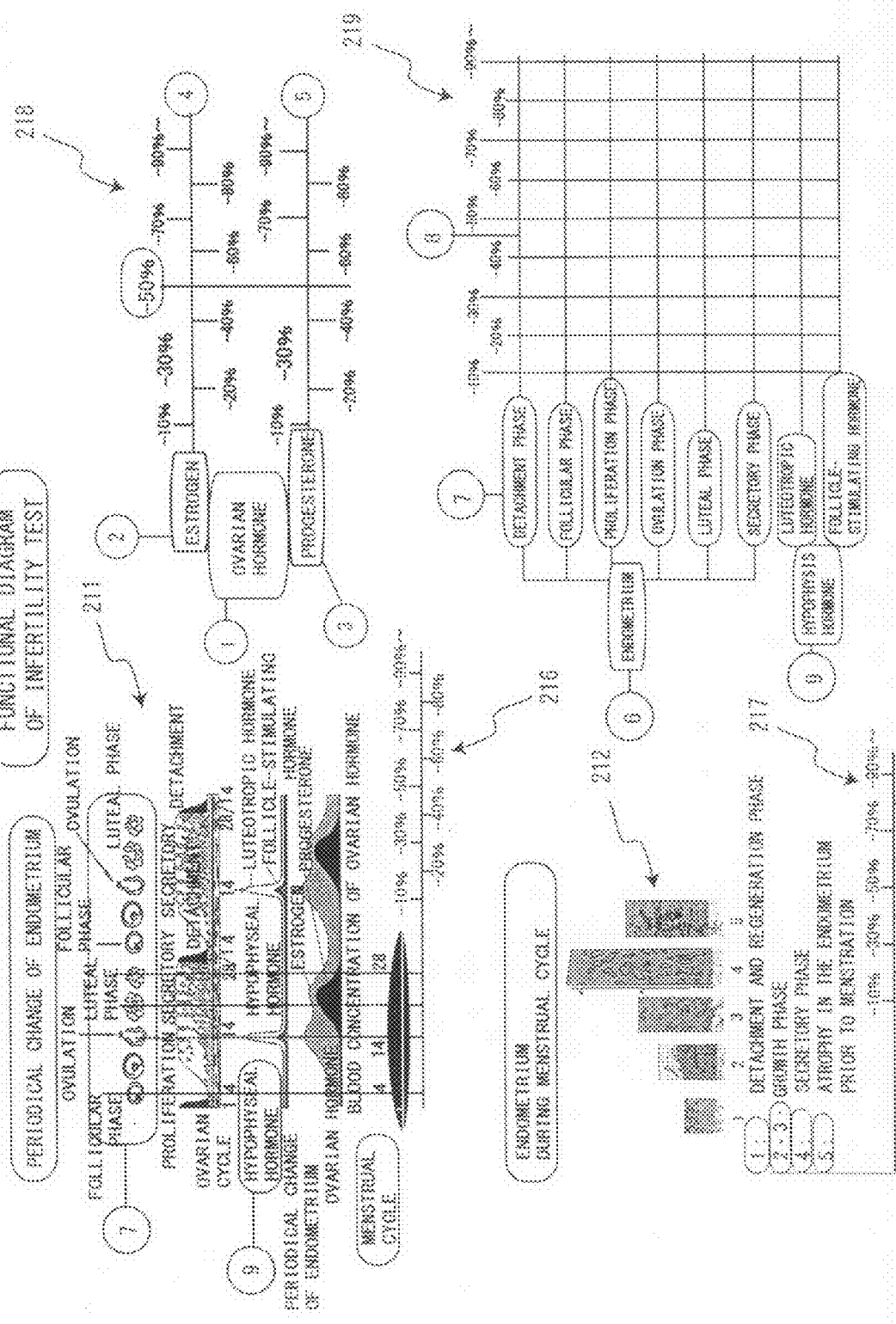
FIG. 21 is a perspective view showing a functional diagram of infertility.

FIG. 21 is an example of the functional diagram for muscle and muscle strength reflex test of the present invention and is a functional diagram of infertility. The functional diagram of infertility is an examination diagram to be used to identify the infertility caused by autonomic disorder and to examine parasympathetic nerves controlling smooth muscles of endometrium. FIG. 21 has image portions 211 and 212 on an upper left and a lower left of the diagram, and further has scale portions 216 to 219 corresponding to each point.

Figure 22:
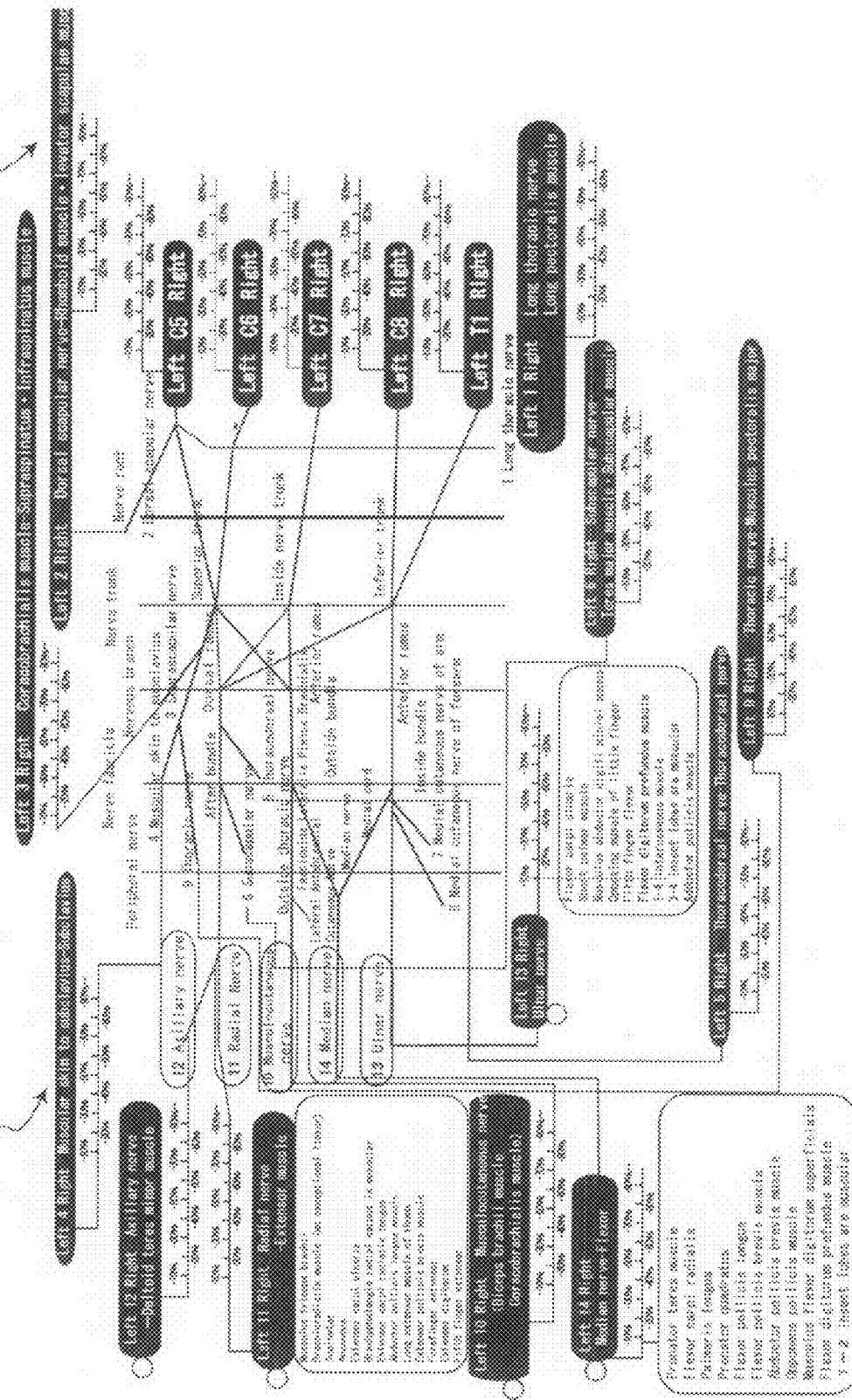
FIG. 22 is a perspective view showing a functional diagram of brachial plexus.

FIG. 22 is an example of the functional diagram for muscle and muscle strength reflex test of the present invention and is a functional diagram of brachial plexus. The functional diagram of brachial plexus is a correlation diagram of nerves controlling the arm, and enables identifying a damaged portion. An image portion 221 describing nerves related to the arm and the correlation of nerves is arranged at a substantial center of the diagram, and a scale portion 226 is arranged around the image portion 221.

Figure 23:
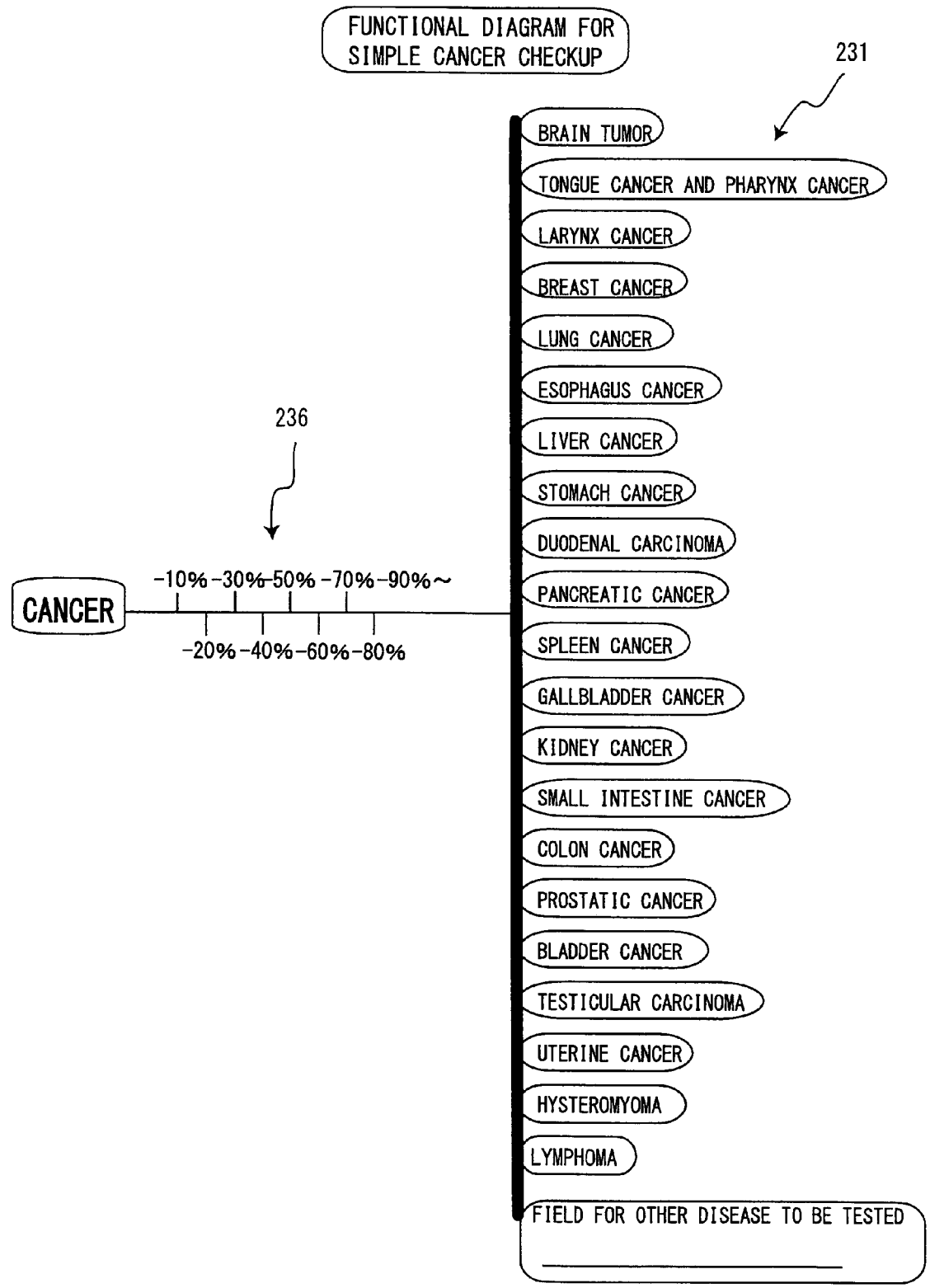
FIG. 23 is a perspective view showing a functional diagram for simple cancer checkup.
Figure 27:
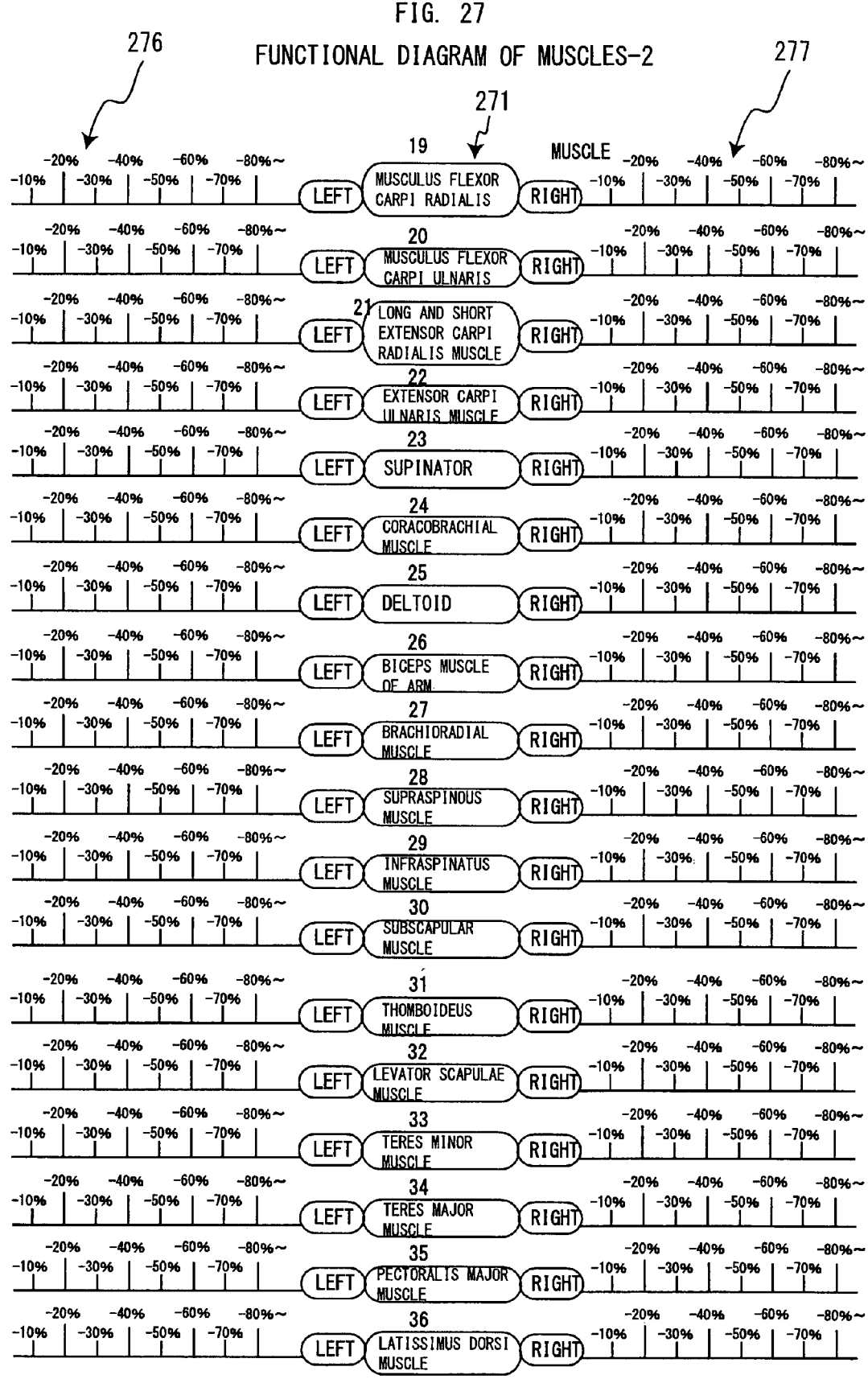
Figure 28:
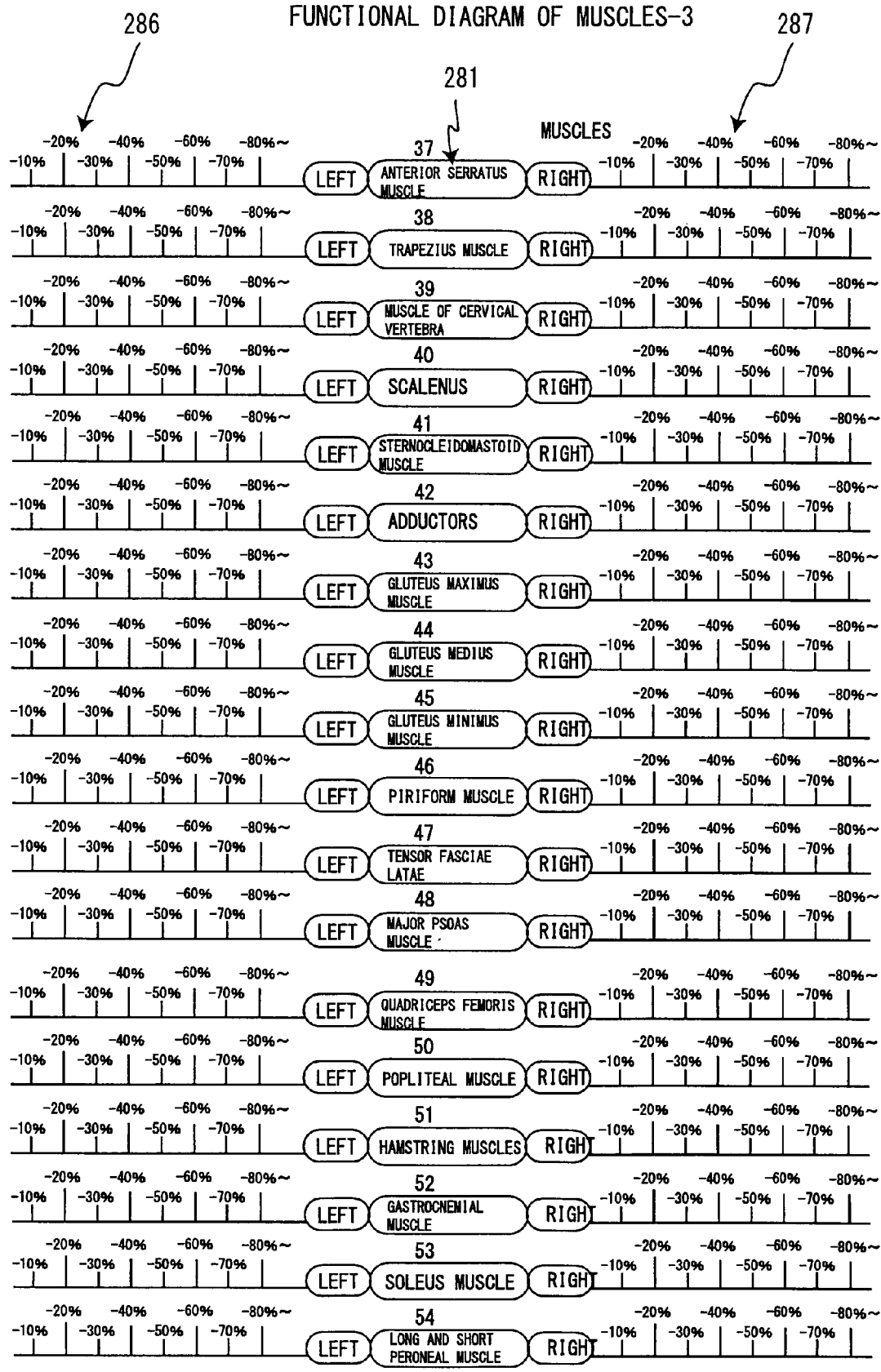
Figure 29:
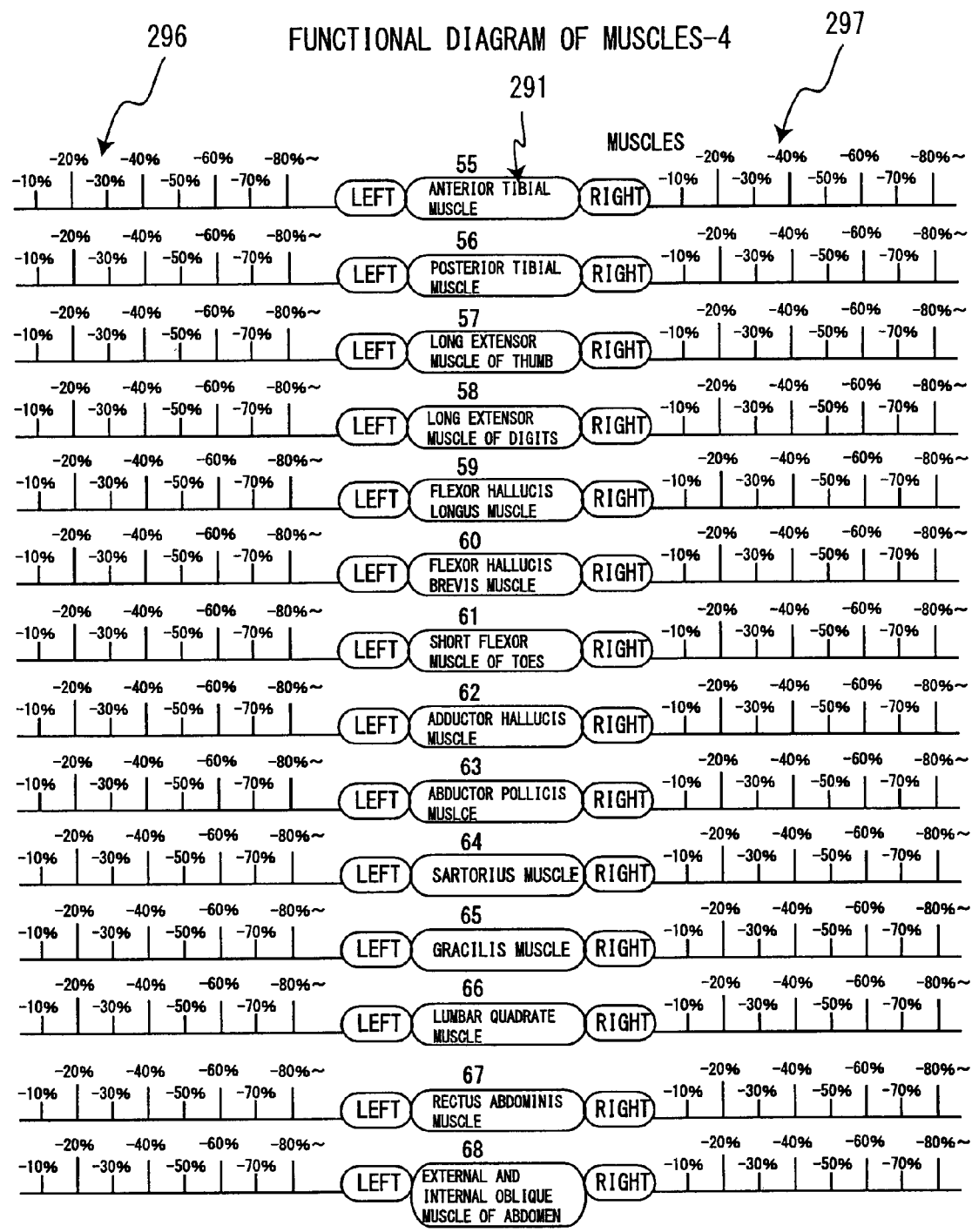

FIG. 23 is an example of the functional diagram for muscle and muscle strength reflex test of the present invention and is a functional diagram for simple cancer checkup. The functional diagram for simple cancer checkup is used to roughly examine which portion has been affected by cancer. An image portion 231 describing various cancers with indications of portions is arranged at the right of the diagram, and a scale portion 236 is arranged at the left of the diagram.

FIG. 24 is an example of the functional diagram for muscle and muscle strength reflex test of the present invention and is a functional diagram for simple health checkup. The functional diagram for simple health checkup is a diagram to be used to easily examine the fitness, the fatigue degree, and the degree of lack of oxygen. The functional diagram for simple health checkup has image portions 241 to 243 indicating items of the examinations and scale portions 246 to 248 respectively corresponding to the image portions 241 to 243.

FIG. 25 is an example of the functional diagram for muscle and muscle strength reflex test of the present invention and is a fatigue display device. A fatigue display device 250 displays following three statuses depending on the degree of the absorbing of oxygen into brain cells, and one of either "OK", "NAP 15", or "DANGER" is switched and displayed on a display unit 251 serving as an image portion. The display may be switched manually by the practitioner, and the display 251 itself may be a device such as a liquid crystal display. The fatigue display device 250 has three indication portions 256, 257, and 258. A case (a) in FIG. 25 shows a normal case where the degree of fatigue is 50% or less, and the degree of fatigue is determined by the muscle reflex test while the patient points at the indication portion 256. A case (b) in FIG. 25 shows a case where the degree of fatigue is 51% to 85%, and the patient need to take a nap for 15 minutes or more. In this case, the muscle reflex test is performed while the patient points at the indication portion 257 to detect the degree of fatigue. A case (c) in FIG. 25 shows a case where the degree of fatigue is 86% or more and substantial sleep is required. In this case, the muscle reflex test is performed while the patient points at the indication portion 258 to detect the degree of fatigue.

FIG. 26 to FIG. 29 are examples of the functional diagram for muscle and muscle strength reflex test of the present invention and are functional diagrams 1 to 4 of muscles. Image portions 261, 271, 281, and 291 are arranged in each of the diagram, and scale portions 266 and 267, 276 and 277, 286 and 287, and 296 and 297 are respectively arranged on either side of the image portions 261, 271, 281, and 291. The use of the functional diagrams 1 to 4 of muscles effectively contributes to the practitioner in that a damaged portion of the patient is identified with high accuracy where the practitioner performs the muscle and muscle strength reflex test.

Figure 30:
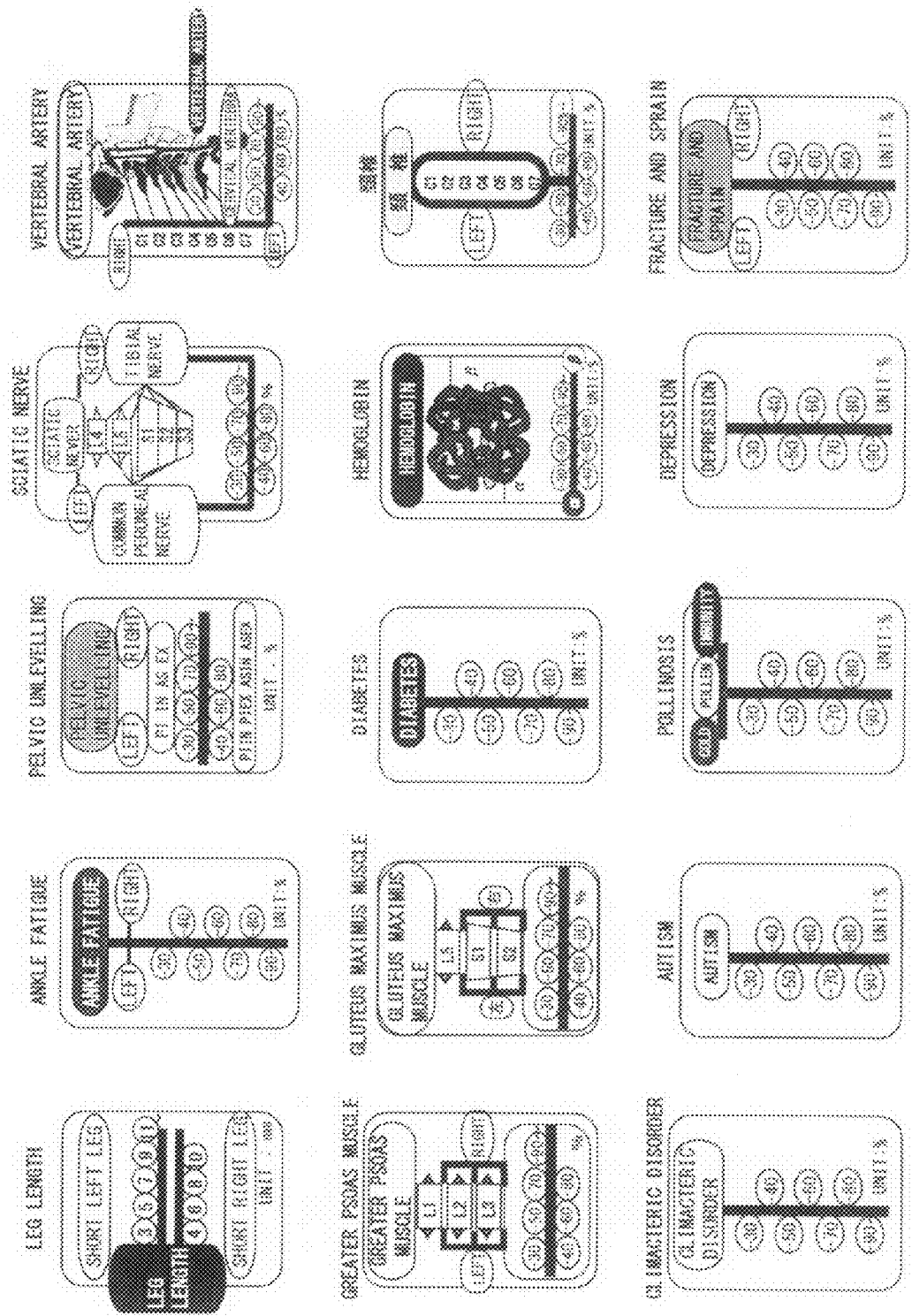
FIG. 30 to FIG. 31 are perspective views showing functional diagrams for cellular phone 1 and 2.
Figure 31:
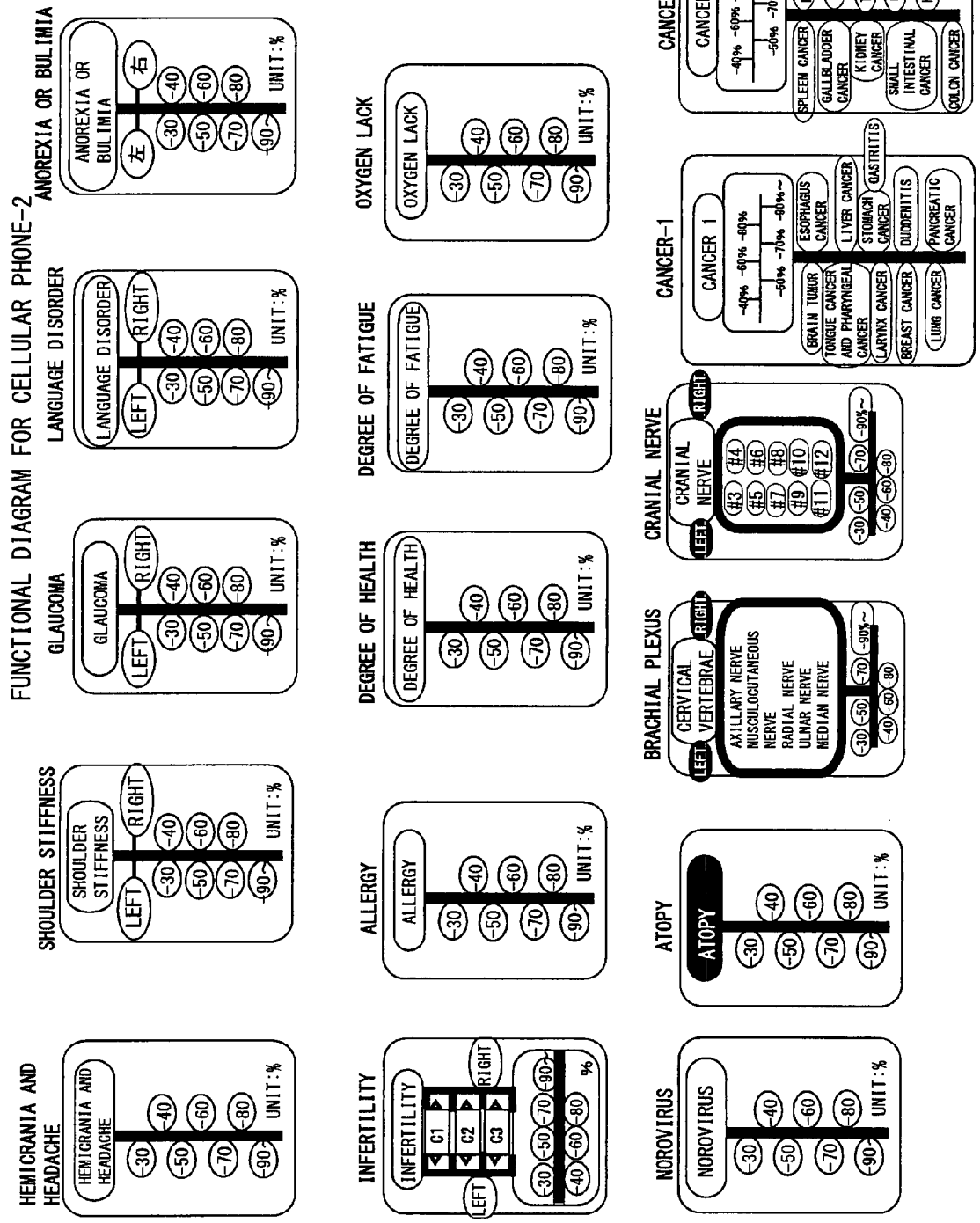

FIG. 30 to FIG. 31 are examples of the functional diagram for muscle and muscle strength reflex test of the present invention and are functional diagrams 1 and 2 for cellular phone. Each of display units 300 represents a display of cellular phone. Examinations using a display of cellular phone can be performed. For example, in a case of FIG. 30, the diabetes can be examined using a combination of an item portion 301 of the diabetes and a scale portion 302 adjacent to the item portion 301, and in a case of FIG. 31, the degree of health can be examined using a combination of an item portion 311 of the degree of health and a scale portion 312 adjacent to the item portion 311.

Figure 32:
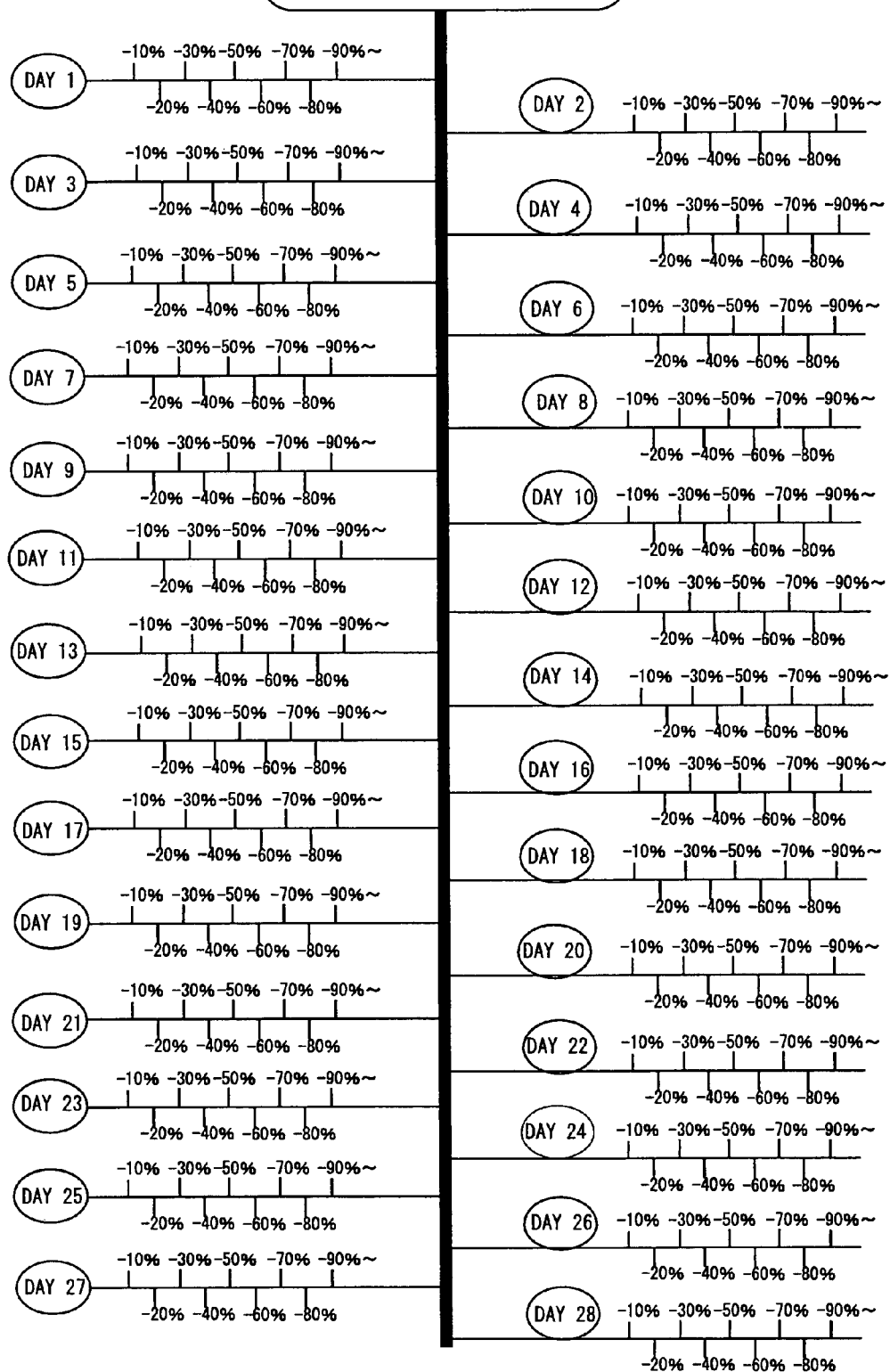
FIG. 32 is a perspective view showing a functional diagram of days of menstrual cycle.

FIG. 32 is an example of the functional diagram for muscle and muscle strength reflex test of the present invention and is a functional diagram of days of menstrual cycle. The functional diagram of days of menstrual cycle is used in the muscle and muscle strength reflex test to accurately grasp the days of menstrual cycle. The patient points at the functional diagram (specimen) with her left index finger (pointing finger), and at the same time, the examiner measures the patient's muscle strength of any one of the right hand, fingers, and arm that is easy to measure. For example, an examination is performed as follows. First, a patient places her left index finger on the first day of the diagram to identify the menstrual day using the functional diagram of days of menstrual cycle. Then, the patient forms a ring shape with her thumb and ring finger, and the examiner tries to force apart the patient's fingers formed in a ring shape, whereas the patient resists the force applied by the examiner, so that the examiner examines the resisting muscle strength of the patient with the muscle and muscle strength reflex test. Subsequently, the patient places her left index finger on the second day, third day, fourth day, and so on, and the above muscle and muscle strength reflex test is repeated. The day where the muscle strength of the patient is the most strong is identified as the menstrual day. If there are two or three days where the muscle strength is strong, the patient then places her left finger on a number of the percentage scale, so that the day where the muscle strength is the most strong is identified.

Figure 33:
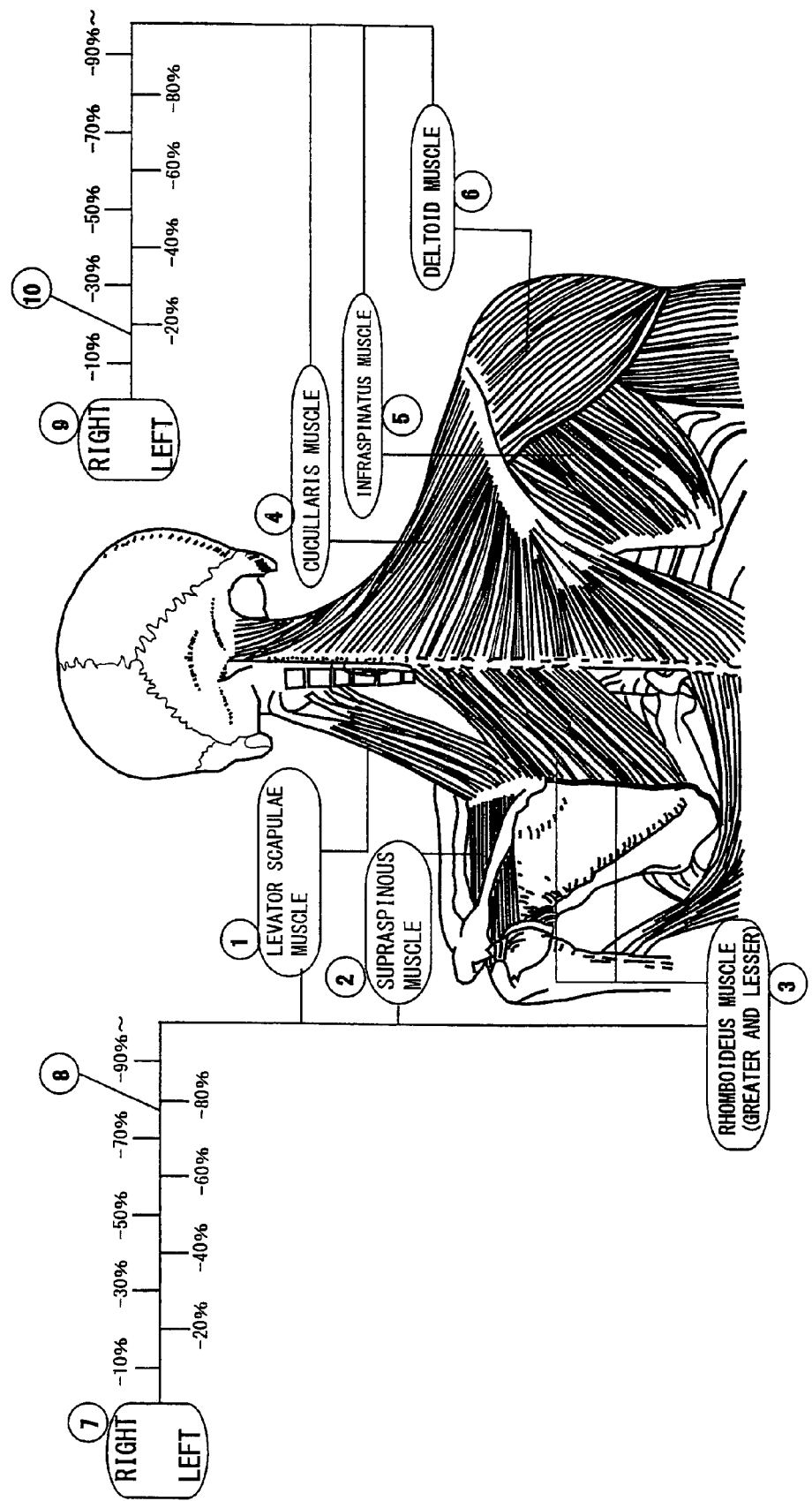
FIG. 33 is a perspective view showing a functional diagram of shoulder muscles.

FIG. 33 is an example of the functional diagram for muscle and muscle strength reflex test of the present invention and is a functional diagram of shoulder muscles. The functional diagram of shoulder muscles is used to examine the function of major muscles of the shoulder. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test. While the examiner examines the patient's muscle strength, the patient places his left index finger on scale portions 1 to 6, one by one, representing muscles. The function of each of the muscles is examined with the muscle reflex test. The muscle whose functionality is recognized to have declined is further examined as to which of the left or right is damaged with the use of numerals 7 and 9. The muscle and muscle strength reflex test is also performed with the use of scale portions 8 and 10 to detect the percentage of functional decline of the examined muscle whose functionality have declined. After the treatment, the muscle and muscle strength reflex test is performed again in a similar manner to confirm whether the treated muscle has been properly adjusted. Finally, the condition of examination and treatment is recorded.

Figure 34:
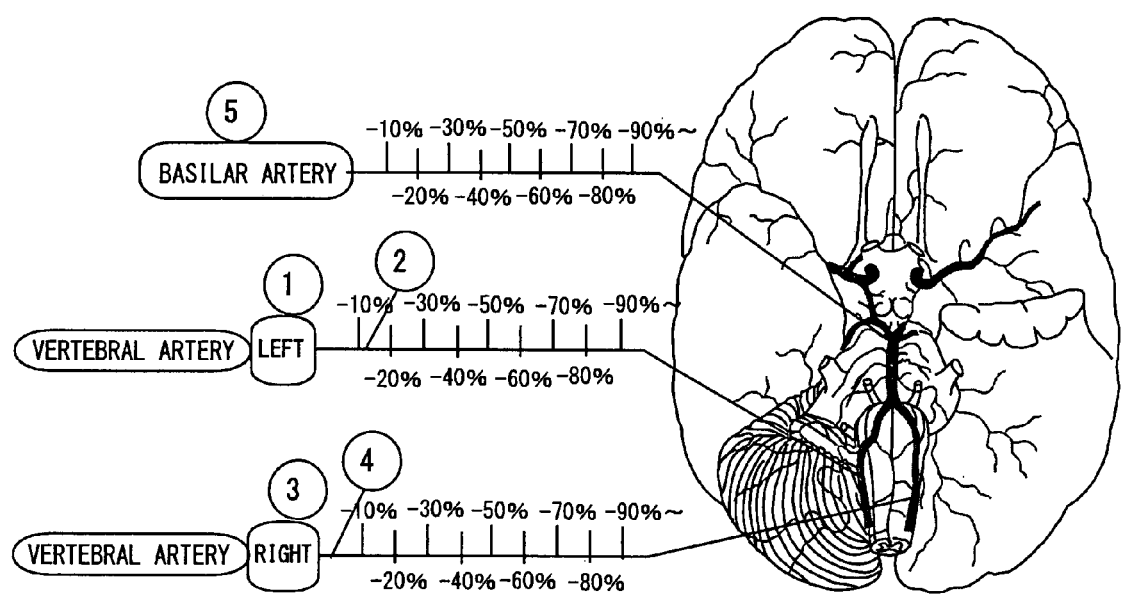
FIG. 34 is a perspective view showing a functional diagram of vertebral artery at the base of brain.

FIG. 34 is an example of the functional diagram for muscle and muscle strength reflex test of the present invention and is a functional diagram of vertebral artery at the base of brain. The functional diagram of vertebral artery at the base of brain is used to grasp the condition of the function of vertebral artery and basilar artery. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test. While the examiner examines the patient's muscle strength, the patient places his left index finger on numerals 1 to 5, one by one, of the diagram each representing a portion of the brain to be examined. The function of each of the portions is examined with the muscle reflex test. The portion whose functionality is recognized to have declined is further examined as to which of the left or right is damaged with the use of numerals 1 and 3. The muscle and muscle strength reflex test is also performed with the use of scale portions 2 and 4 to detect the percentage of functional decline of the examined portion whose functionality have declined. After the treatment, the muscle and muscle strength reflex test is performed again in a similar manner to confirm whether the treated portion has been properly adjusted. Finally, the condition of examination and treatment is recorded.

Figure 35:
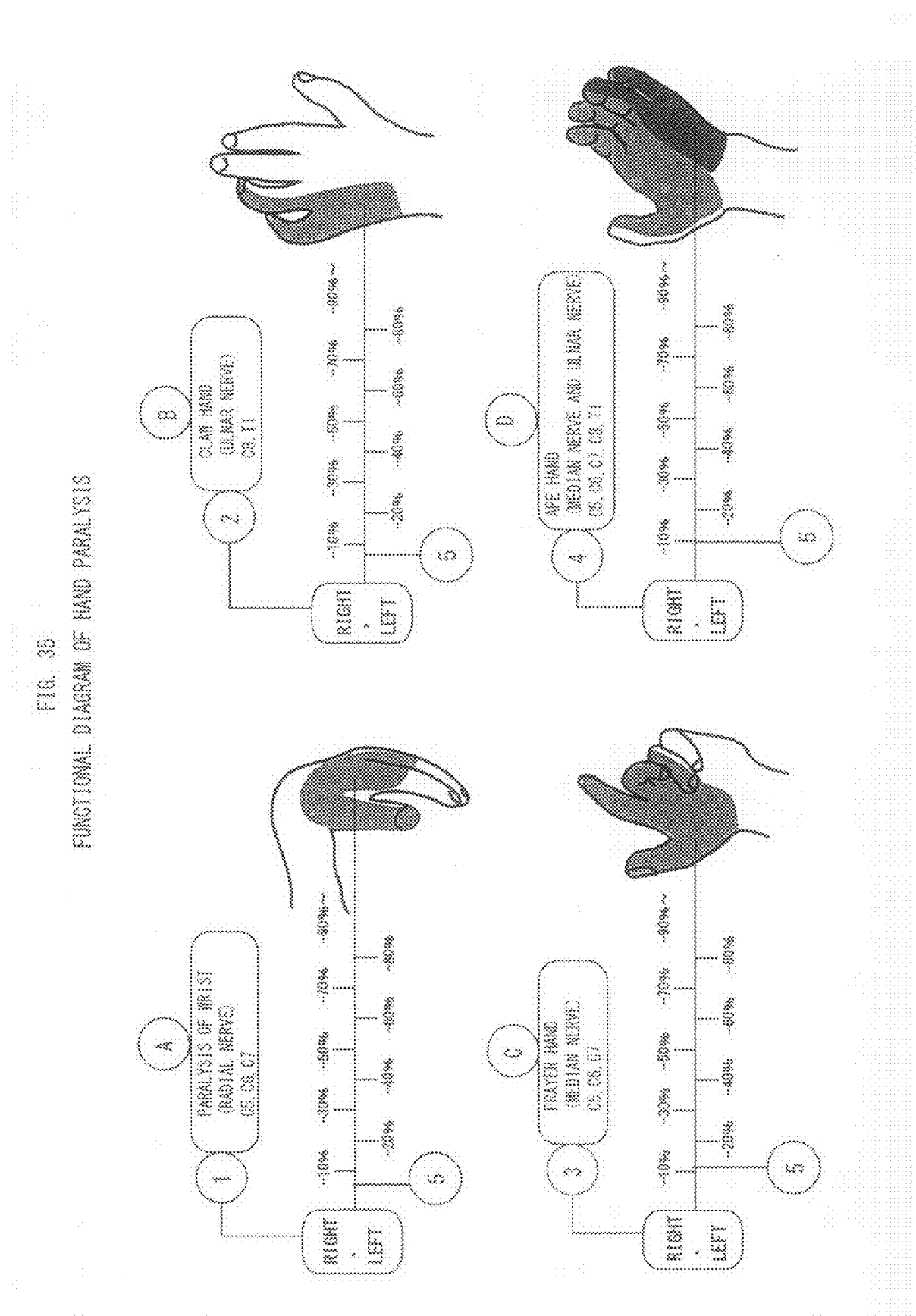
FIG. 35 is a perspective view showing a functional diagram of hand paralysis.

FIG. 35 is an example of the functional diagram for muscle and muscle strength reflex test of the present invention and is a functional diagram of hand paralysis. The functional diagram of hand paralysis is used to grasp the condition of hand paralysis. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test. While the examiner examines the patient's muscle strength, the patient places his left index finger on alphabets A to D, one by one, of the diagram each representing a portion of the hand to be examined. The function of each of the portions is examined with the muscle reflex test. The portion whose functionality is recognized to have declined is further examined as to which of the left or right is damaged with the use of numerals 1 to 4. The muscle and muscle strength reflex test is also performed with the use of scale portions 5 to detect the percentage of functional decline of the examined portion whose functionality have declined. After the treatment, the muscle and muscle strength reflex test is performed again in a similar manner to confirm whether the treated portion has been properly adjusted. Finally, the condition of examination and treatment is recorded.

Figure 36:
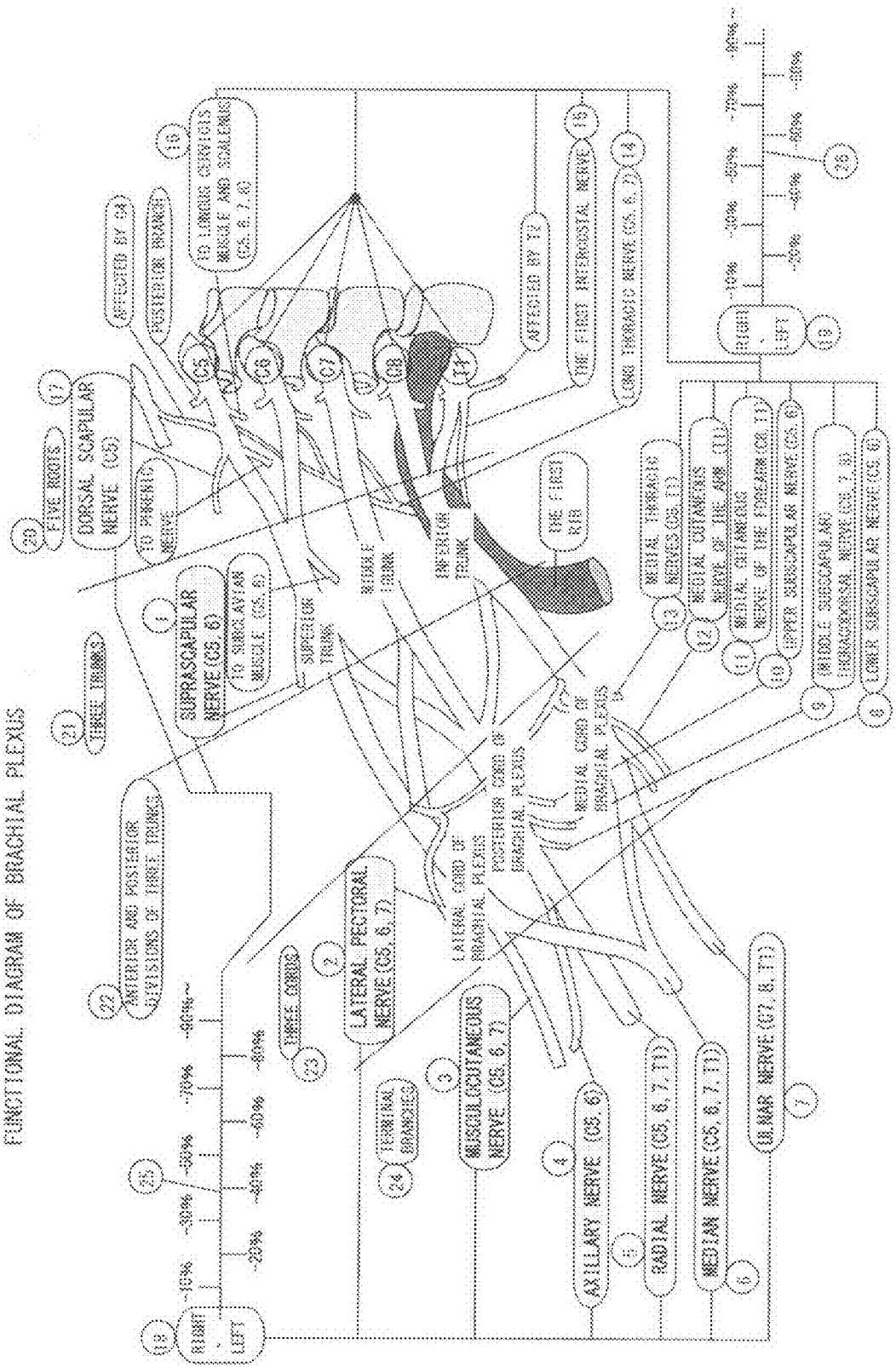
FIG. 36 is a perspective view showing a functional diagram of brachial plexus.

FIG. 36 is an example of the functional diagram for muscle and muscle strength reflex test of the present invention and is a functional diagram of brachial plexus. The functional diagram of brachial plexus is used to grasp the condition of the function of shoulder and arm. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test. While the examiner examines the patient's muscle strength, the patient places his left index finger on portions 1 to 17 of the diagram, one by one, each representing a never of the shoulder and arm to be examined. The function of each of the nerves is examined with the muscle reflex test. The nerve whose functionality is recognized to have declined is further examined as to which of the left or right is damaged with the use of numerals 18 to 19. The muscle and muscle strength reflex test is also performed with the use of scale portions 25 and 26 to detect the percentage of functional decline of the examined portion whose functionality have declined. After the treatment, the muscle and muscle strength reflex test is performed again in a similar manner to confirm whether the treated portion has been properly adjusted. The muscle and muscle strength reflex test is also performed with the use of numerals 20 to 24 to examine which level causes a functional decline. Finally, the condition of examination and treatment is recorded.

Figure 37:
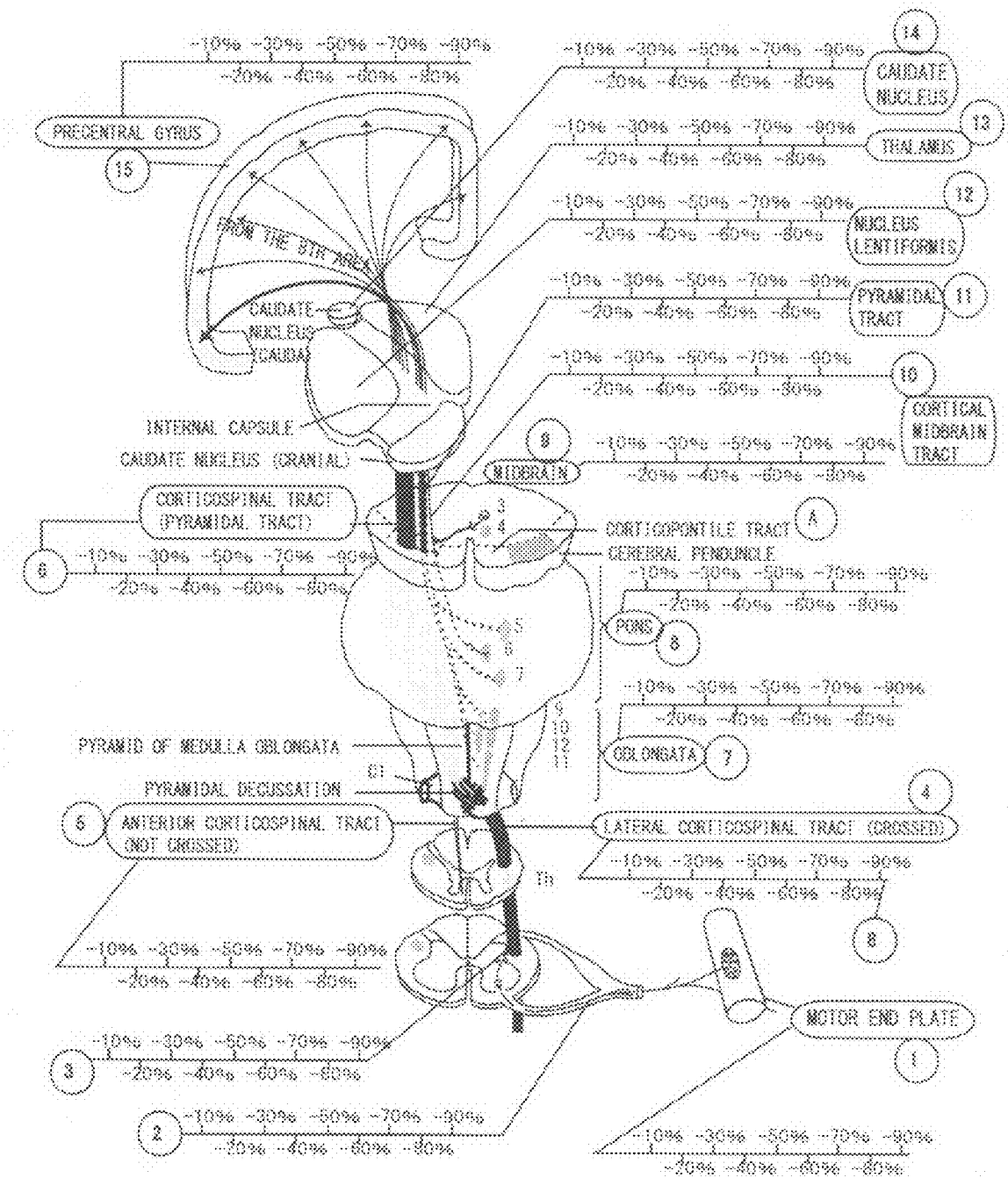
FIG. 37 is a perspective view showing a functional diagram of travel of pyramidal tract.

FIG. 37 is an example of the functional diagram for muscle and muscle strength reflex test of the present invention and is a functional diagram of travel of pyramidal tract. The functional diagram of pyramidal tract is used to grasp the condition of the function of each portion from peripheral nerves to the precentral gyrus. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test. While the examiner examines the patient's muscle strength, the patient places his left index finger on portions 1 to 15 of the diagram, one by one. The function of each of the nerves is examined with the muscle reflex test. The muscle and muscle strength reflex test is also performed with the use of scale portions 1 and 15 to detect the percentage of functional decline of the examined portion whose functionality have declined. After the treatment, the muscle and muscle strength reflex test is performed again with the use portions 1 to 15 in a similar manner to confirm whether the treated portion has been properly adjusted. The muscle and muscle strength reflex test is also performed with the use of numerals 1 to 15 to examine which level causes the functional decline. Finally, the condition of examination and treatment is recorded. A detailed examination is not required. It is sufficient to merely know which level is recognized to be abnormal.

Figure 38:
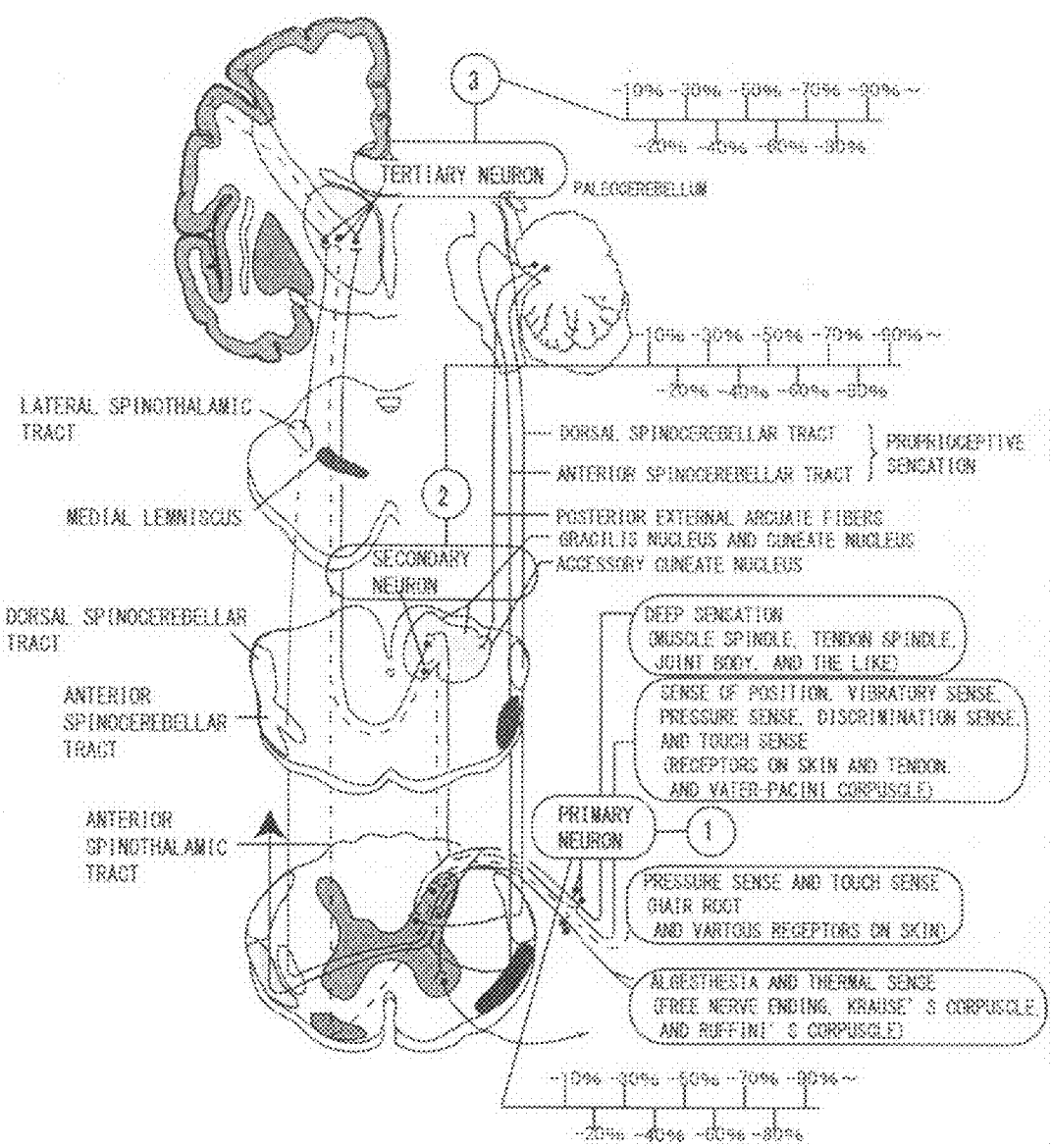
FIG. 38 is a perspective view showing a functional diagram of pyramidal tract.

FIG. 38 is an example of the functional diagram for muscle and muscle strength reflex test of the present invention and is a functional diagram of travel of pyramidal tract. The functional diagram of travel of pyramidal tract displays the transmission from perception receptors at the end and is used to identify a damaged portion in levels 1, 2, and 3. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test. While the examiner examines the patient's muscle strength, the patient places his left index finger on portions 1 to 3, one by one, of the diagram each representing a portion of pyramidal tract to be examined. The function of each of the nerves is examined with the muscle reflex test. The muscle and muscle strength reflex test is also performed with the use of scale portions 1 and 3 to detect the percentage of functional decline of the examined portion whose functionality have declined. After the treatment, the muscle and muscle strength reflex test is performed again in a similar manner to confirm whether the treated portion has been properly adjusted. The muscle and muscle strength reflex test is also performed with the use of numerals 1 to 3 to examine which level causes the functional decline. Finally, the condition of examination and treatment is recorded. A detailed examination is not required. It is sufficient to merely know which level is recognized to be abnormal. The importance of the upper cervical vertebrae is understood from this functional diagram of the motor nervous system and the perception nervous system.

Figure 39:
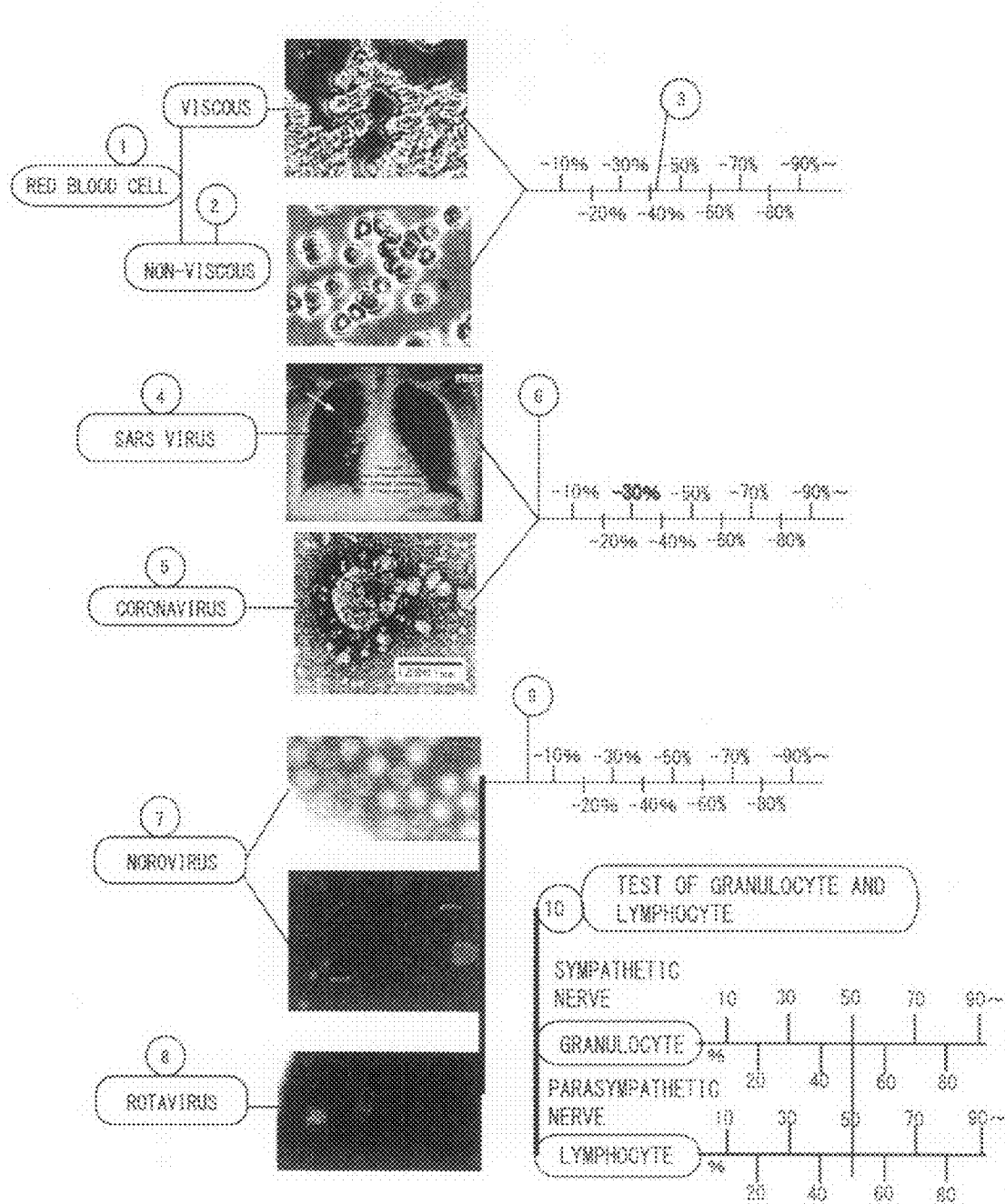
FIG. 39 is a perspective view showing a functional diagram of virus.

FIG. 39 is an example of the functional diagram for muscle and muscle strength reflex test of the present invention and is a functional diagram of virus. The functional diagram of virus is used to easily examine the virus infection of the patient. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test. While the examiner examines the patient's muscle strength, the patient places his left index finger on portions 1, 4, 5, 7, 8, and 10, one by one, of the diagram each representing a virus to be examined. The infection to each of the viruses is examined with the muscle reflex test. The muscle and muscle strength reflex test is also performed with the use of scale portions 3, 6, 9, and 10 to detect the percentage of functional decline with respect to the virus possibly infecting the patient. If the functional decline is determined to be more than −30%, the patient should be presumed to be infected with the virus and treated carefully, and the examiner should ask the patient to undergo examination at a medical institution. After the treatment, the muscle and muscle strength reflex test is performed again in a similar manner to confirm whether the treated portion has been properly adjusted. The muscle and muscle strength reflex test is also performed with the use of numerals 4, 5, 7, and 8 to examine which level causes the functional decline, and The muscle and muscle strength reflex test is also performed with the use of numerals 6, 9, and 10 to examine whether the immune strength is recovered. If the granulocyte and lymphocyte are found to be less than −50% at the numeral 10, the examiner should be cautious and ask the patient to undergo examination at a medical institution. After the treatment, an examination should be performed with the numerals 6 and 9. If the muscle reflex test determines that the muscle strength is less than −30%, it should be considered that the patient is infected with virus, and the examiner should introduce the patient to a medical institution. Finally, the condition of examination and treatment is recorded. A detailed examination is not required.

Figure 40:
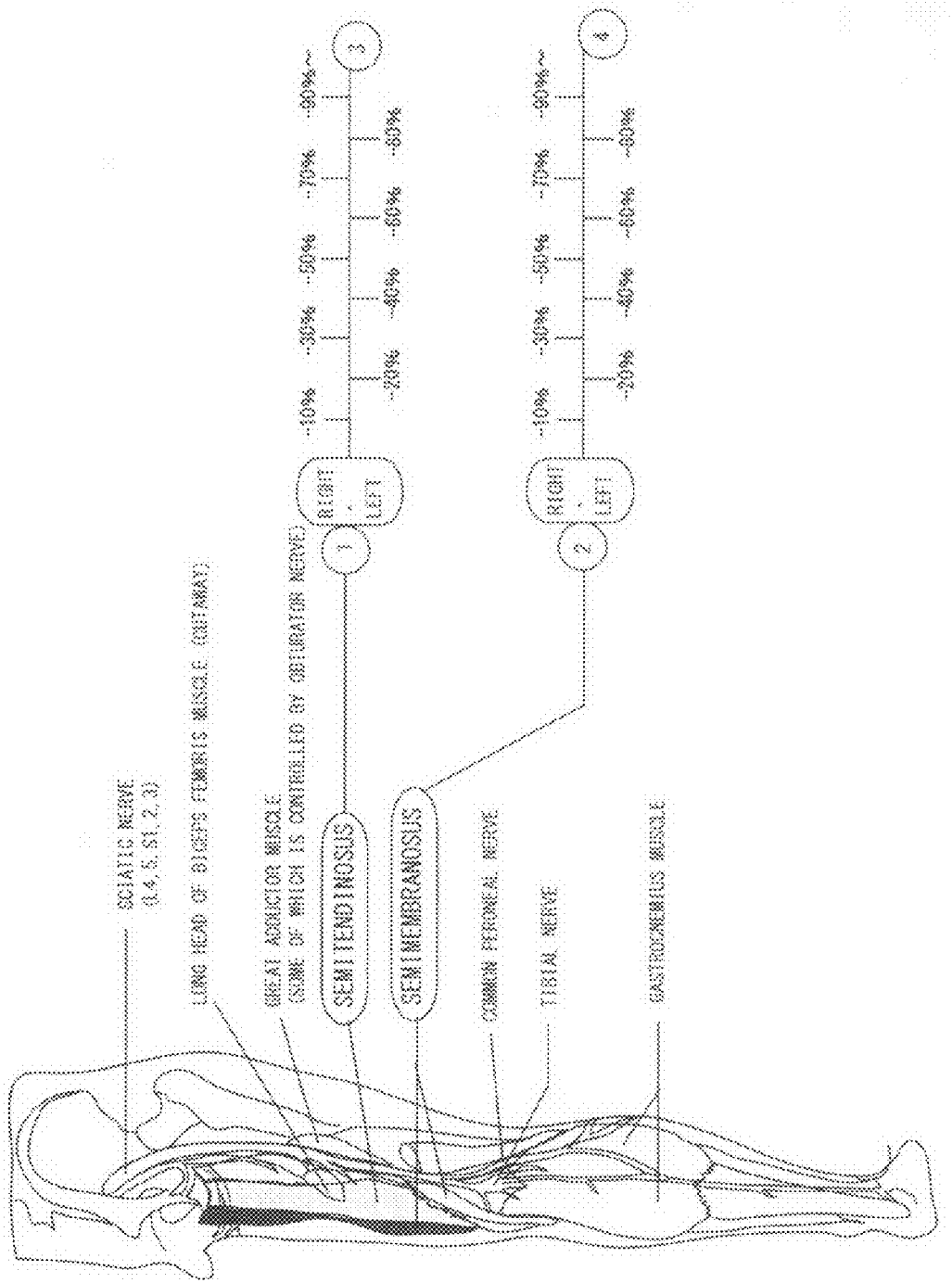
FIG. 40 is a perspective view showing a functional diagram of semitendinosus and semimembranosus.

FIG. 40 is an example of the functional diagram for muscle and muscle strength reflex test of the present invention and is a functional diagram of semitendinosus and semimembranosus. The functional diagram of semitendinosus and semimembranosus is used to examine the functional decline of semitendinosus and semimembranosus. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test. While the examiner examines the patient's muscle strength, the patient places his left index finger on portions 1 and 2, one by one, of the diagram each representing a portion of the patient's body to be examined. The function of each portion is examined with the muscle and muscle strength reflex test. The muscle and muscle strength reflex test is also performed with the use of scale portions 3 and 4 to detect the percentage of functional decline of the examined portion whose functionality have declined. After the treatment, the muscle and muscle strength reflex test is performed again in a similar manner to confirm whether the treated portion has been properly adjusted. Finally, the condition of examination and treatment is recorded.

Figure 41:
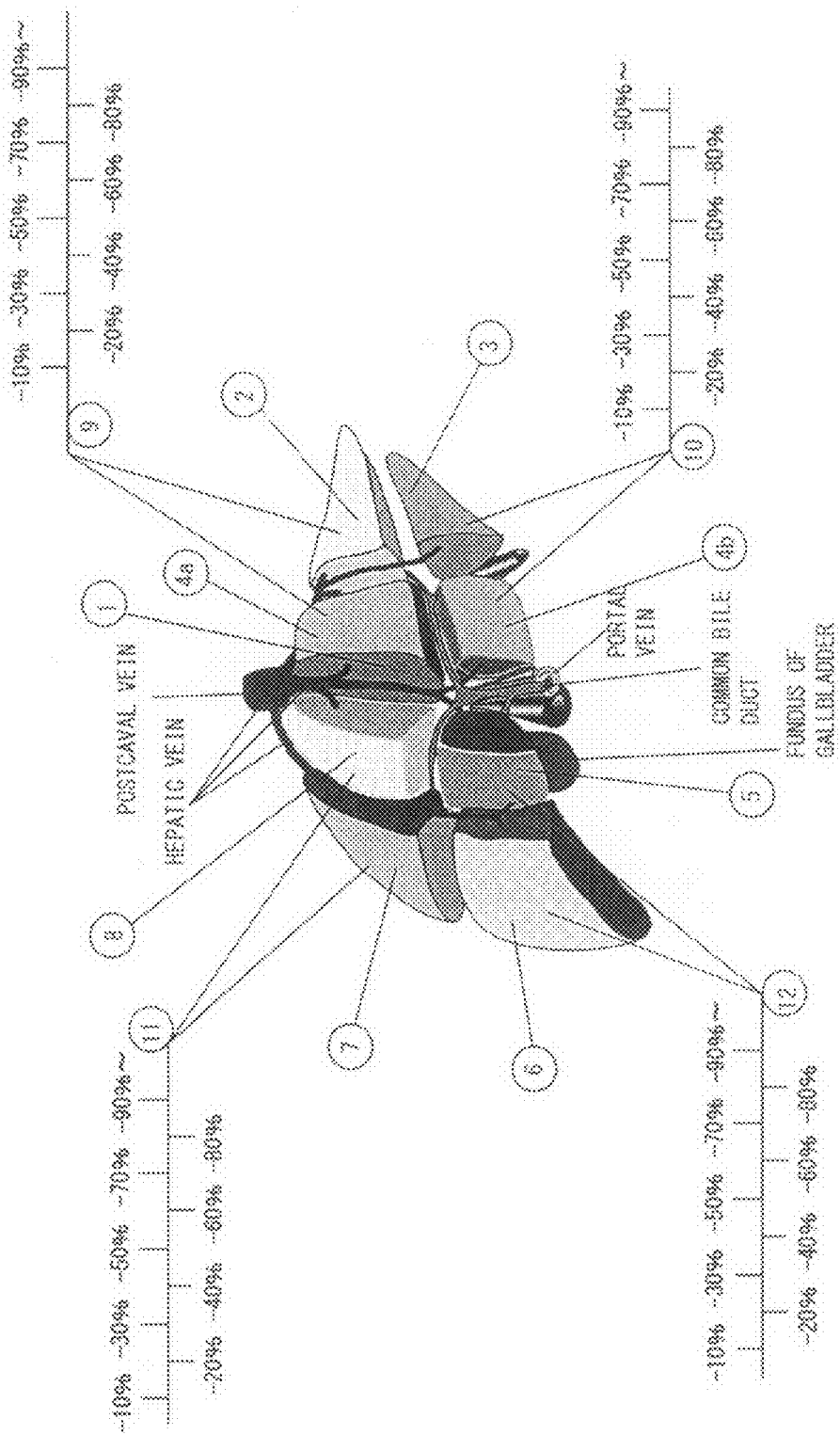
FIG. 41 is a perspective view showing a functional diagram of liver.

FIG. 41 is an example of the functional diagram for muscle and muscle strength reflex test of the present invention and is a functional diagram of liver. The functional diagram of liver is used to examine the functional decline of liver. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test. While the examiner examines the patient's muscle strength, the patient places his left index finger on portions 1 to 8, one by one, of the diagram each representing a portion of the patient's body to be examined. The function of each portion is examined with the muscle and muscle strength reflex test. The muscle and muscle strength reflex test is also performed with the use of scale portions 9, 10, 11, and 12 to detect the percentage of functional decline of the examined portion whose functionality have declined. After the treatment, the muscle and muscle strength reflex test is performed again in a similar manner to confirm whether the treated portion has been properly adjusted. Finally, the condition of examination and treatment is recorded.

Figure 42:
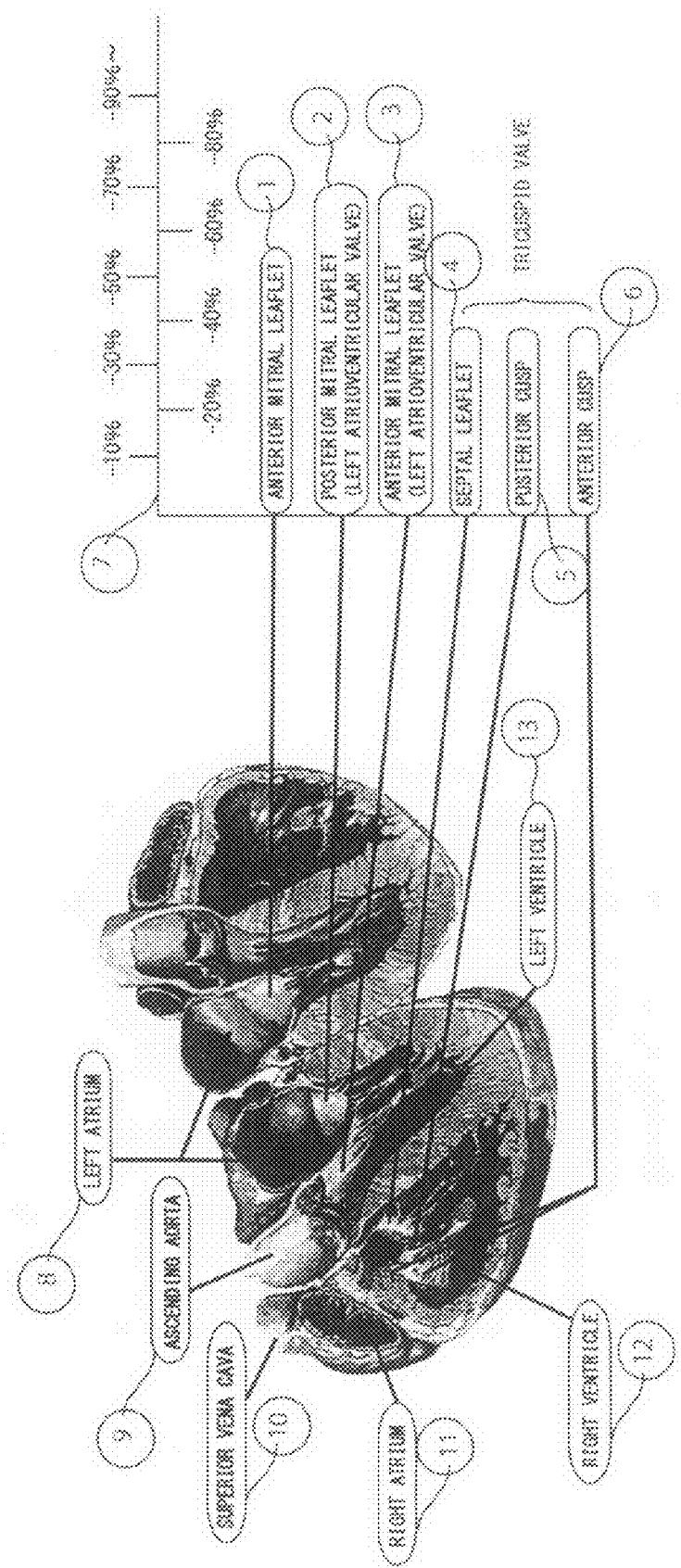
FIG. 42 is a perspective view showing a functional diagram of heart valve.

FIG. 42 is an example of the functional diagram for muscle and muscle strength reflex test of the present invention and is a functional diagram of heart valve. The functional diagram of heart valve is used to examine the functional decline of heart valve. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test. While the examiner examines the patient's muscle strength, the patient places his left index finger on portions 1 to 13, one by one, of the diagram each representing a portion of the patient's body to be examined. The function of each portion is examined with the muscle and muscle strength reflex test. The muscle and muscle strength reflex test is also performed with the use of scale portion 7 to detect the percentage of functional decline of the examined portion whose functionality have declined. After the treatment, the muscle and muscle strength reflex test is performed again in a similar manner to confirm whether the treated portion has been properly adjusted. Finally, the condition of examination and treatment is recorded.

FIG. 43 is an example of the functional diagram for muscle and muscle strength reflex test of the present invention and is a blank functional diagram for a simple examination. Examination items are written to this blank functional diagram for a simple examination so that a new functional diagram is created. Names of symptoms, medicines, and muscles are written to the title of examination of the cards 1 and 2 so that a new functional diagram is created.

FIG. 44 is an example of the functional diagram for muscle and muscle strength reflex test of the present invention and is a functional diagram of coronary artery of heart. The functional diagram of coronary artery of heart is used to examine the functional decline of coronary artery of heart. The patient points at the functional diagram (specimen) with his left index finger (pointing finger), and at the same time, the examiner measures the muscle strength of any one of the right hand, fingers, and arm of the patient that is easy to measure. For example, an examination using the functional diagram is performed as follows. First, a patient forms a ring shape with his thumb and ring finger with his right hand. Then, the examiner tries to force apart the patient's fingers formed in a ring shape, whereas the patient resists the force applied by the examiner, so that the examiner examines the resisting muscle strength of the patient with the muscle and muscle strength reflex test.

While the examiner examines the patient's muscle strength, the patient places his left index finger on portions 1 to 6, one by one, of the diagram each representing a portion of the patient's body to be examined. The function of each portion is examined with the muscle and muscle strength reflex test. The muscle and muscle strength reflex test is also performed with the use of a scale portion 7 to detect the percentage of functional decline of the examined portion whose functionality has been determined to have declined. After the treatment, the muscle and muscle strength reflex test is performed again in a similar manner to confirm whether the treated portion has been properly adjusted. Finally, the condition of examination and treatment is recorded.

The functional diagram of the present invention can be applied to portions of the entire body and enables identify a damaged portion with the use of pictures, illustrations, letters, anatomical charts, and the like. The functional diagram enables the practitioner to easily grasp unknown diseases and the reason of the disease based on assumption. Furthermore, a new functional diagram can be created for an expected portion or disease.

The above-described functional diagrams of the present invention shows examples where discrete numbers are arranged on the graduation of the scale. However, the graduation can also have other expressions such as heavy, light, normal, abnormal, alphabets, and the like indicating some other orders. Furthermore, the graduation of the scale is straight in the above-described examples, but the scale can also be a curved, wave, staggered, and matrix shape.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

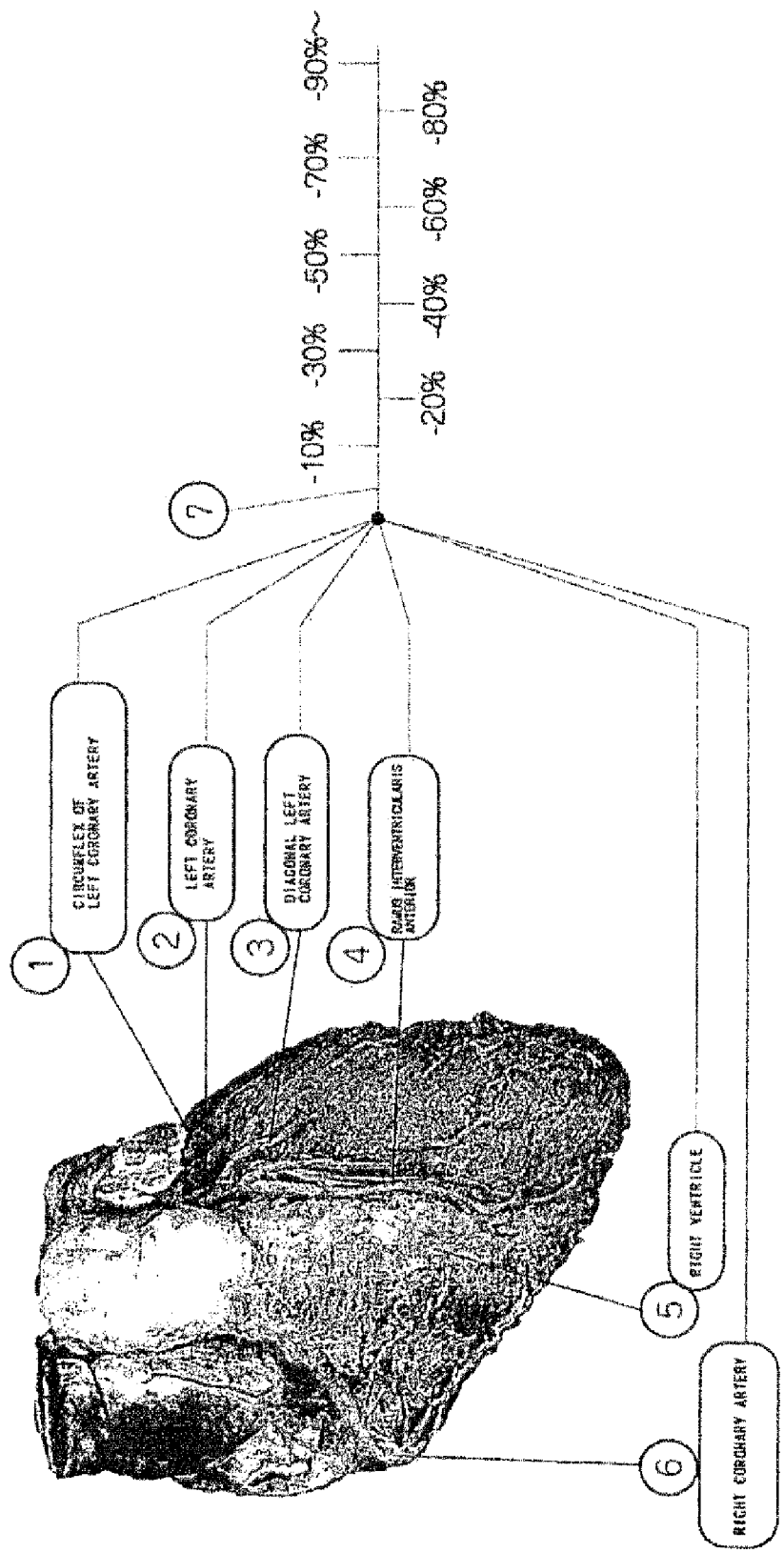

What is claimed is:

1. A functional diagram for a muscle and muscle strength reflex test comprising:
   an image portion identifying a prescribed examination item; and a scale portion arranged adjacent to the image portion and having a scale representing a degree of the examination item, wherein
   a patient touches a portion of the scale to undergo a first muscle and muscle strength reflex test, and then, the patient touches a different portion of the scale depending on a result of the first muscle and muscle strength reflex test to undergo a second muscle and muscle strength reflex test.

2. An examination method for examining a patient with the use of a functional diagram for a muscle and muscle strength reflex test, to examination method comprising the steps of:
   having a patient touch a portion of the functional diagram representing a portion or symptom of his body with one of his fingers of one of his hands; and
   having a patient undergo the muscle and muscle strength reflex test to examine the portion or symptom of his body represented by the portion of the functional diagram touched by the patient.

3. The examination method according to claim 2, wherein the functional diagram comprises:
   an image portion representing the portion or symptom of his body; and
   a scale portion arranged adjacent to the image portion and having a scale representing a degree of a damage of the portion or symptom.

4. The examination method according to claim 2, wherein the muscle and muscle strength reflex test comprises the steps of:
   having the patient form an O-Ring shape with the other of his hands by placing the fingertips of his thumb and one of his remaining fingers together; and
   attempting to pull apart the O-Ring shape to measure a muscle strength of the fingers.

5. The examination method according to claim 2, wherein the patient touches a plurality of portions of the functional diagram, one by one, and the muscle and muscle strength reflex test is performed to determine a muscle strength at each of the plurality of the portions, so that the muscle strength at each of the plurality of the portions can be compared with each other.

* * * * *

UNITED STATES PATENT AND TRADEMARK OFFICE
CERTIFICATE OF CORRECTION

| | |
|---|---|
| PATENT NO. | : 7,506,544 B2 |
| APPLICATION NO. | : 11/775645 |
| DATED | : March 24, 2009 |
| INVENTOR(S) | : Kihachirou Takano |

It is certified that error appears in the above-identified patent and that said Letters Patent is hereby corrected as shown below:

The drawing sheet, consisting of Fig. 44, should be deleted to be replaced with the drawing sheet, consisting of Fig. 44, as shown on the attached pages.

Signed and Sealed this

Tenth Day of November, 2009

David J. Kappos
*Director of the United States Patent and Trademark Office*